United States Patent
Xiao et al.

(10) Patent No.: US 11,796,499 B2
(45) Date of Patent: Oct. 24, 2023

(54) IMMOBILIZATION STRATEGIES FOR ENHANCING SENSITIVITY OF ELECTROCHEMICAL APTAMER-BASED SENSORS

(71) Applicants: Yi Xiao, Cary, NC (US); Yingzhu Liu, Wuhan (CN); Juan Canoura, Hialeah Gardens, FL (US)

(72) Inventors: Yi Xiao, Cary, NC (US); Yingzhu Liu, Wuhan (CN); Juan Canoura, Hialeah Gardens, FL (US)

(73) Assignee: THE FLORIDA INTERNATIONAL UNIVERSITY BOARD OF TRUSTEES, Miami, FL (US)

( * ) Notice: Subject to any disclaimer, the term of this patent is extended or adjusted under 35 U.S.C. 154(b) by 0 days.

(21) Appl. No.: 18/065,118

(22) Filed: Dec. 13, 2022

(65) Prior Publication Data
US 2023/0213471 A1 Jul. 6, 2023

Related U.S. Application Data

(60) Provisional application No. 63/288,882, filed on Dec. 13, 2021.

(51) Int. Cl.
*G01N 27/327* (2006.01)
*G01N 33/543* (2006.01)
*G01N 33/53* (2006.01)

(52) U.S. Cl.
CPC ..... *G01N 27/3276* (2013.01); *G01N 27/3277* (2013.01); *G01N 33/5308* (2013.01); *G01N 33/5438* (2013.01)

(58) Field of Classification Search
CPC .......... G01N 27/3276; G01N 27/3277; G01N 33/5308; G01N 33/5438
See application file for complete search history.

(56) References Cited

PUBLICATIONS

Y. Liu, Immobilization Strategies for Enhancing Sensitivity of Electrochemical Aptamer-Based Sensors, ACS Appl. Mater. Interfaces 2021(13), p. 9491-99). (Year: 2021).*

B.R. Baker, An electronic, Aptamer-Based Small-Molecule Sensor for the Rapid, Label-Free Detection of Cocaine in Adulterated Samples and Biological Fluids, J. Am. Chem. Soc. 2006(128), p. 3138-39. (Year: 2006).*

K.S. Sykes, Measuring Practical Reversibility of Surface-Bound DNA for Mechanistic Insight into Folding-Based Sensors, J. Electrochem. Soc. 2021(168), 116511. (Year: 2021).*

(Continued)

*Primary Examiner* — Caitlyn Mingyun Sun
(74) *Attorney, Agent, or Firm* — SALIWANCHIK, LLOYD & EISENSCHENK

(57) ABSTRACT

The subject invention provides methods for fabricating electrochemical aptamer-based (E-AB) sensors with enhanced sensitivity, signal-to-noise ratios, LOD, and improved stability and reproducibility. The subject invention also provides methods for aptamer immobilization on the surface of the electrode, which favors sufficient spacing between aptamers at the microscale to achieve optimal target recognition, folding, and signal transduction. The E-AB sensors of the subject invention provide superior sensing regardless of the sequence or structure of the bound aptamers or the physiochemical properties of the target.

15 Claims, 17 Drawing Sheets
Specification includes a Sequence Listing.

(56) References Cited

PUBLICATIONS

Y. Liu, Tuning Biosensor Cross-Reactivity Using Aptamer Mixtures, Anal. Chem. 2020(92), p. 5041-47. (Year: 2020).*

K.S. Sykes and R. J. White, Measuring Practical Reversibility of Surface-Bound DNA for Mechanistic Insight into Folding-Based Sensors, J. Electrochem. Soc. 2021,168, 116511, p. 1-8. (Year: 2021).*

Y. Liu, Tuning Biosensors Cross-Reactivity Using Aptamer Mixtures, Analytical Chemistry, 2020 (92), p. 5041-47. (Year: 2020).*

Akbarian, Mohsen et al. "Biological aspects in controlling angiogenesis: current progress." Cellular and Molecular Life Sciences 79(7):1-35, Jun. 7, 2022.

Alsaiari, Norah Salem et al. "The Application of Nanomaterials for the Electrochemical Detection of Antibiotics: A Review." Micromachines 12(3):1-33, Mar. 15, 2021.

Azizi, Sajad et al. "Carbon dots-thionine modified aptamer-based biosensor for highly sensitive cocaine detection." Journal of Electroanalytical Chemistry 907, pp. 1-9, (Year: 2022).

Bilibana, Mawethu Pascoe et al. "Aptamers functionalized hybrid nanomaterials for algal toxins detection and decontamination in aquatic system: Current progress, opportunities, and challenges." Ecotoxicology and Environmental Safety 232, pp. 1-15, (Year: 2022).

Chen, Zhi-Min et al. "Real-Time Tunable Dynamic Range for Calibration-Free Biomolecular Measurements with a Temperature-Modulated Electrochemical Aptamer-Based Sensor in an Unprocessed Actual Sample." Anal. Chem. 94(2):1397-1405, (Year: 2022).

Feng, Chao et al. "Temperature-regulated non-monotonic behavior of DNA immobilization on poly(N-isopropylacrylamide) (PNIPAm)-grafted surface." Colloids and Surfaces A: Physicochemical and Engineering Aspects 640, pp. 1-9, (Year: 2022).

Fu, Xiaochen et al. "Fabrication strategies for metal-organic framework electrochemical biosensors and their applications." Coordination Chemistry Reviews 475, pp. 1-21, (Year: 2023).

Gu, Qufei et al. "Hybridization and self-assembly behaviors of surface-immobilized DNA in close proximity: A single-molecule perspective." Aggregate e186. pp. 1-12, Feb. 6, 2022.

Jia, Wenchao et al. "Evaluation the effect of nanoparticles on the structure of aptamers by analyzing the recognition dynamic of aptamer functionalized nanoparticles." Analytica Chimica Acta 1183, pp. 1-10, (Year 2021).

Kaili, Chang et al. "Aptamers as Recognition Elements for Electrochemical Detection of Exosomes." Chem. Res. Chinese Universities 38(4): 879-885, (Year: 2022).

Li, Xin et al. "Electrochemical Conjugation of Aptamers on a Carbon Fiber Microelectrode Enables Highly Stable and Selective In Vivo Neurosensing." Angew. Chem. Int. Ed. 61(42):1-6, Aug. 12, 2022.

Li, Ling et al. "Development of a colorimetric aptasensor fabricated with a group-specific aptamer and AuNPs@Fe2+ nanozyme for simultaneous detection of multiple diarrheic shellfish poisons." Talanta 246, pp. 1-8, (Year: 2022).

Li, Guiyin et al. "Highly Senstive Electrochemical Aptasensor for Detection of glypican-3 Using Hemin-Reduced Graphene Oxide-Platinum Nanoparticles Coupled with Conductive Reduced Graphene Oxide-Gold Nanoparticles." Journal of Biomedical Nanotechnology 17(12):2444-2454 (Year 2021).

Liao, Dongyun et al. "Design an efficient photoelectrochemical aptasensor for PCB72 based on CdTe@CdS core@shell quantum dots-decorated TiO2 nanotubes." Journal of Hazardous Materials 441, pp. 1-12, (Year: 2023).

Onaş, Andra Mihaela et al. "Critical Design Factors for Electrochemical Aptasensors based on Target-Induced Conformational Changes: The Case of Small-Molecule Targets." Biosensors 12(10):1-31, Oct. 1, 2022.

Sanford, Aimee A. et al. "Combating small molecule environmental contaminants: detection and sequestration using functional nucleic acids." Chemical Science 13(26):7670-7684, (Year: 2022).

Somayeh, Sahraneshin Samani et al. "A novel electrochemical biosensor for detection of micrococcal nuclease in milk based on an U-shaped DNA structure." Talanta 253 pp. 1-9, (Year: 2023).

Sykes, Kiana S. & White, Ryan J. "Effects of Nucleic Acid Structural Heterogeneity on the Electrochemistry of Tethered Redox Molecules." Langmuir 38, pp. 7322-7330, (Year: 2022).

Sykes, Kiana S. & White, Ryan J. "Measuring Practical Reversibility of Surface-Bound DNA for Mechanistic Insight into Folding-Based Sensors." Journal of The Electrochemical Society 168(11): 1-8, (Year: 2021).

Tran, Thanh Tam Toan et al. "A state-of-the-art review of graphene-based nanomaterials to determine antibiotics by electrochemical techniques." Environmental Research 208, pp. 1-8, (Year: 2021).

Zhang, Jiayu et al. "A facile aptamer-based sensing strategy for dopamine detection through the fluorescence energy transfer between dye and single-wall carbon nanohorns." Spectrochimica Acta Part A: Molecular and Biomolecular Spectroscopy 279, pp. 1-8, (Year: 2022).

* cited by examiner

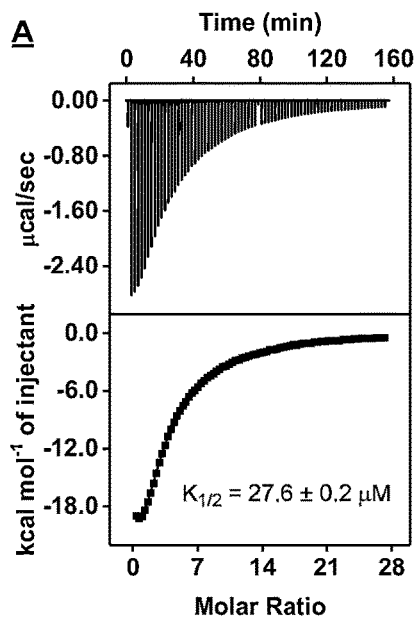
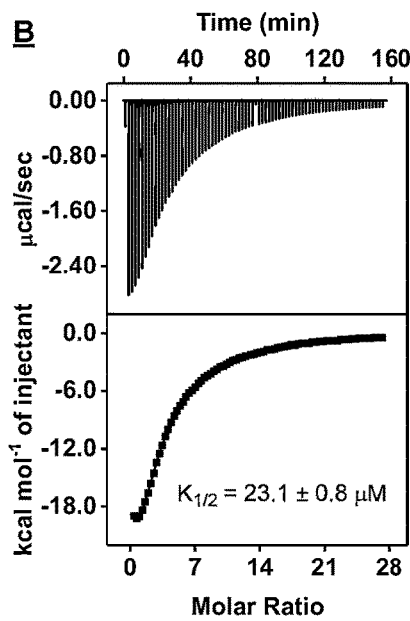
FIG. 1A
FIG. 1B
FIG. 2A
FIG. 2C
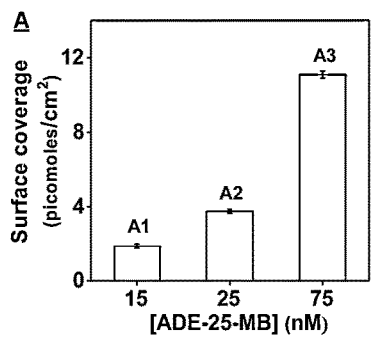
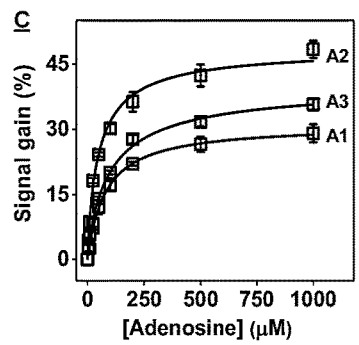
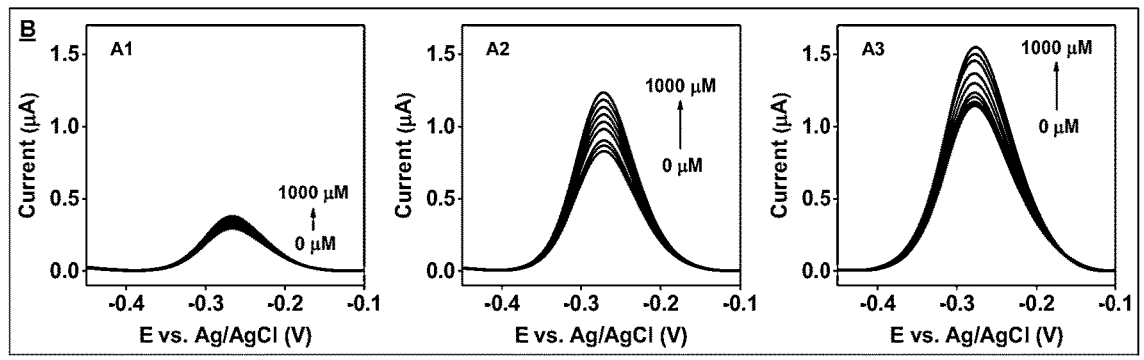
FIG. 2B FIG. 6A  FIG. 6B  FIG.6C
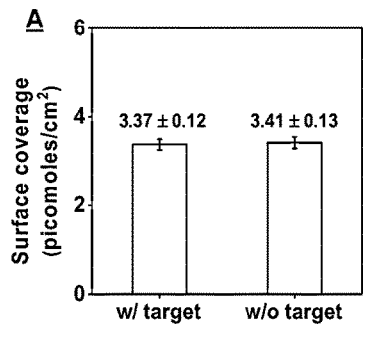 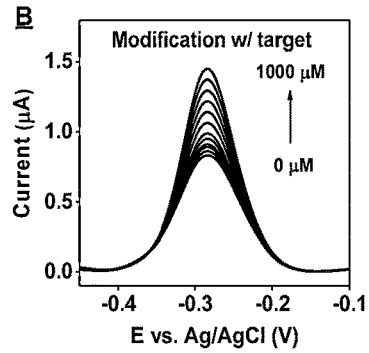 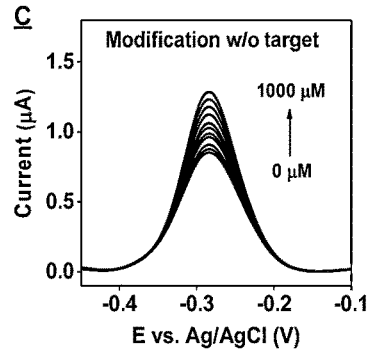
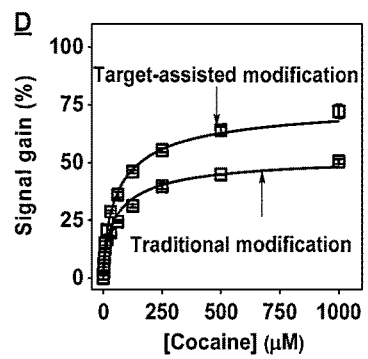 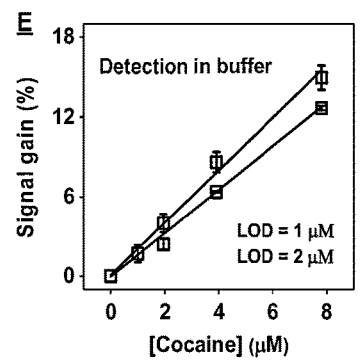
FIG. 6D  FIG. 6E
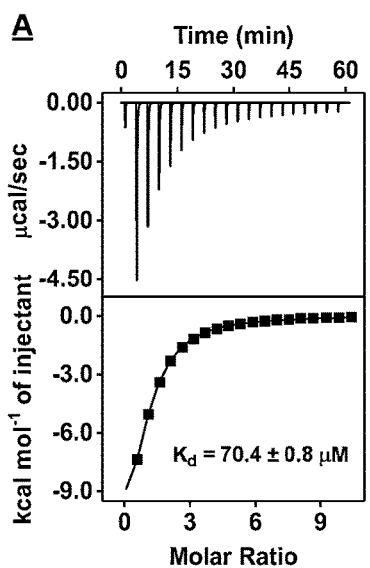 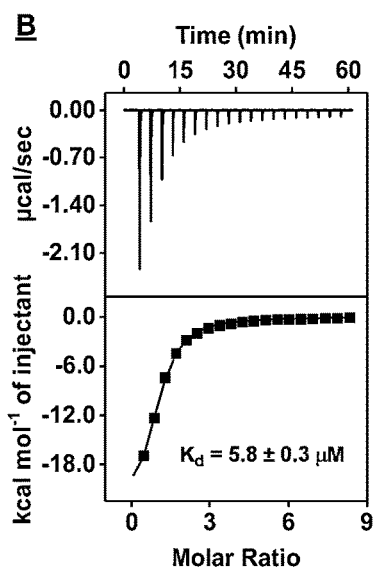 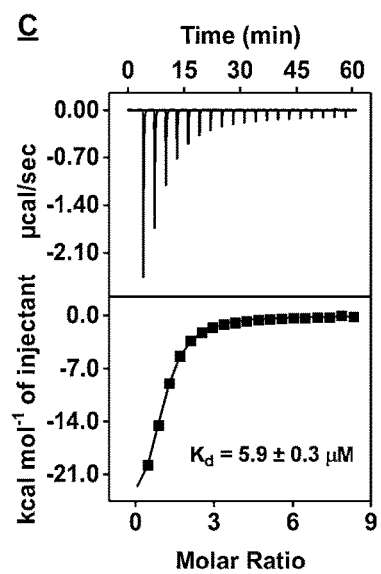
FIG. 7A  FIG. 7B  FIG. 7C FIG. 10A
FIG. 10B
FIG. 10C
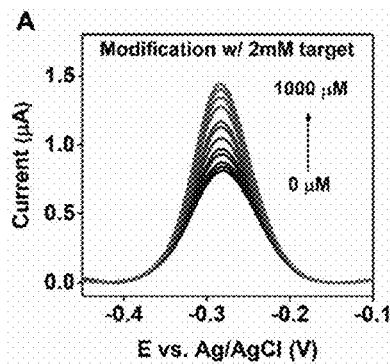
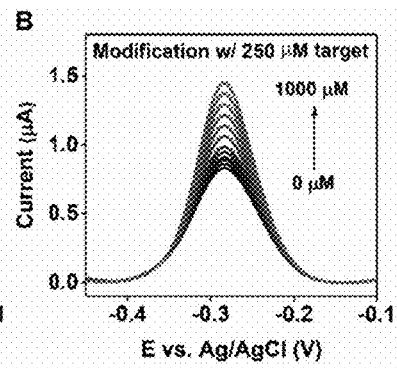
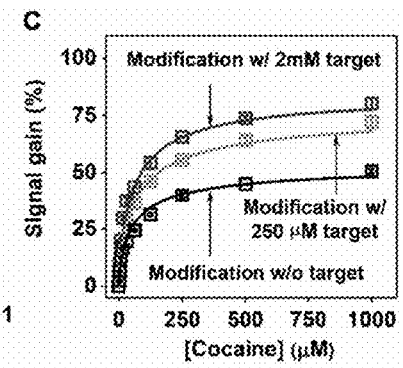
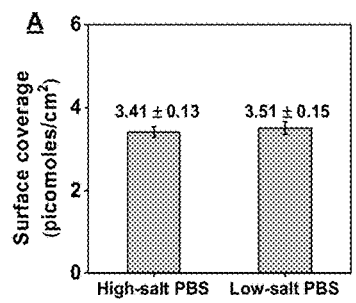
FIG. 10D
FIG. 11A
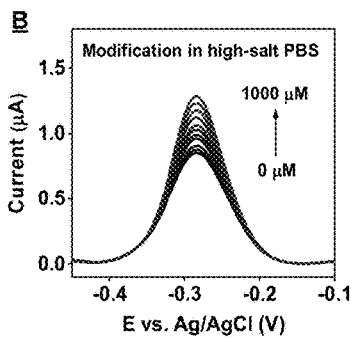
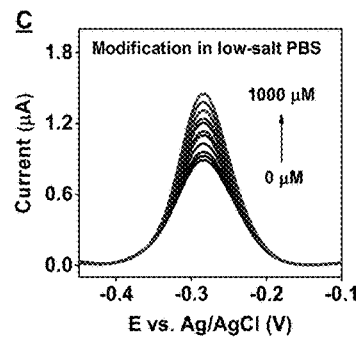
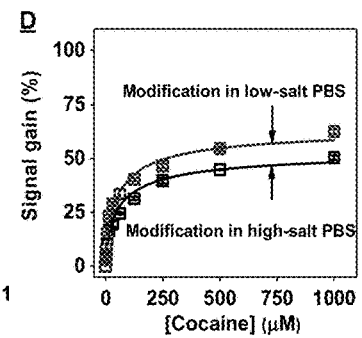
FIG. 11B
FIG. 11C
FIG. 11D

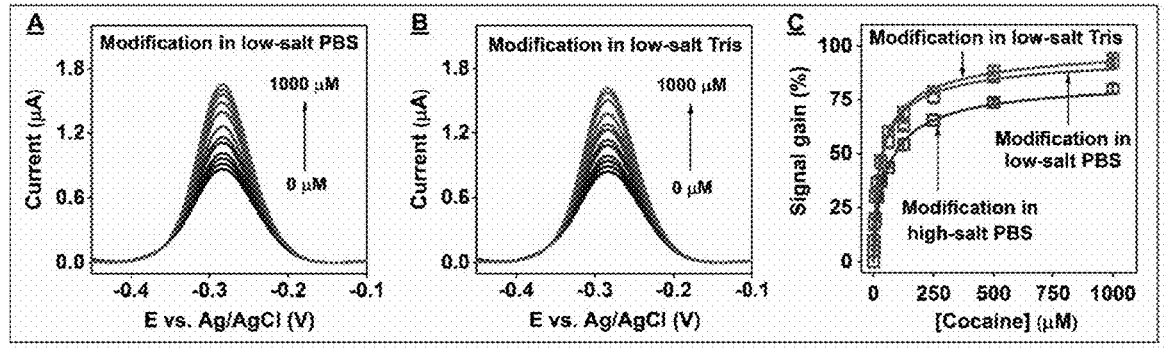
FIG. 14A    FIG. 14B    FIG. 14C
FIG. 14D    FIG. 14E    FIG. 14F
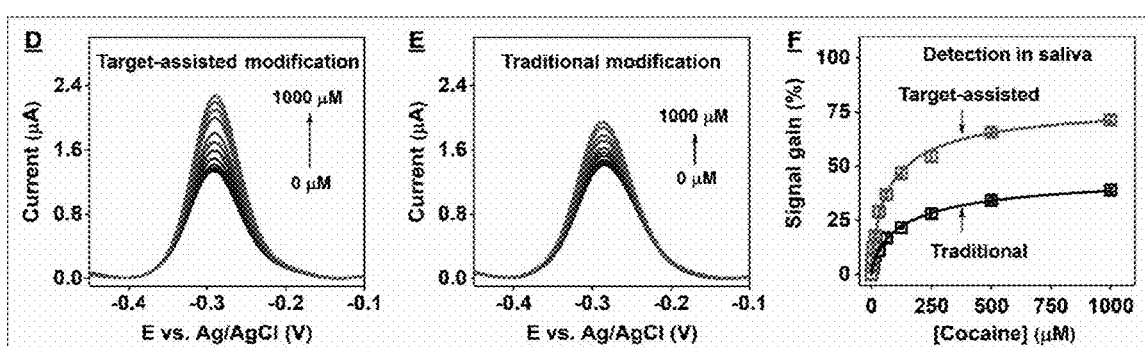
FIG. 14G

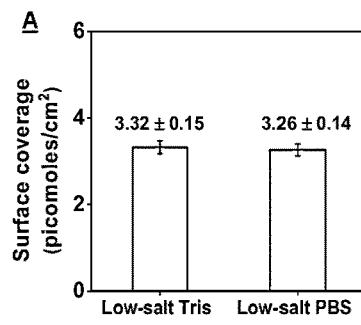
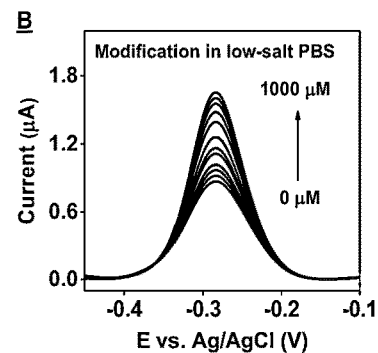
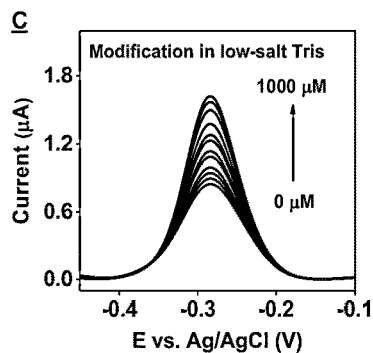
FIG. 15A  FIG. 15B  FIG. 15C
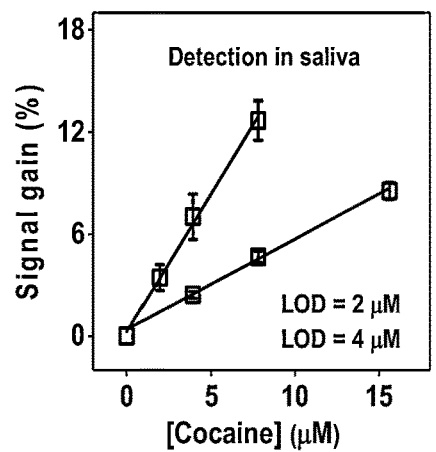
FIG. 16
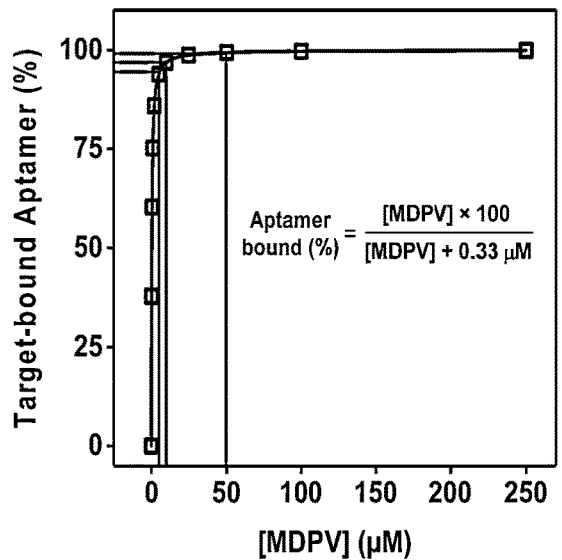
FIG. 17

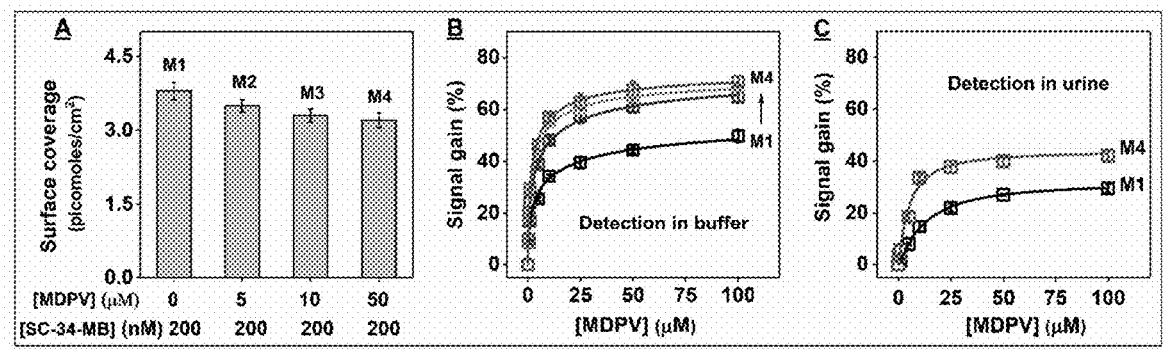
FIG. 18A     FIG. 18B     FIG. 18C
FIG. 18D     FIG. 18E     FIG. 18F
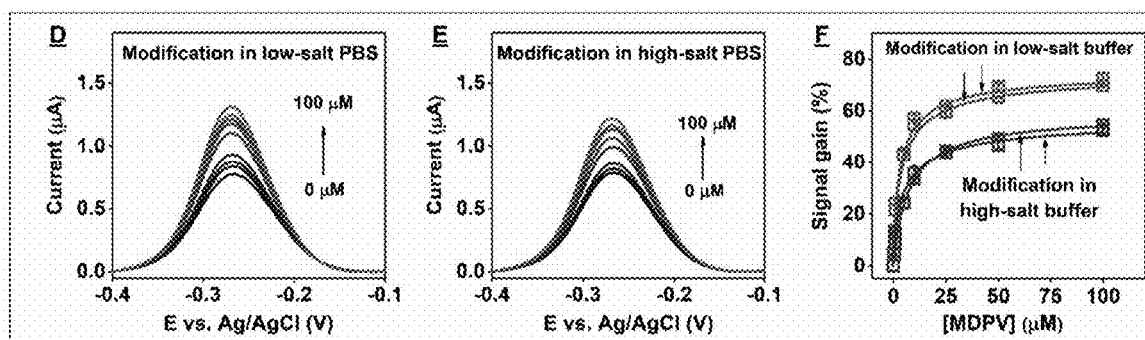
FIG. 18G

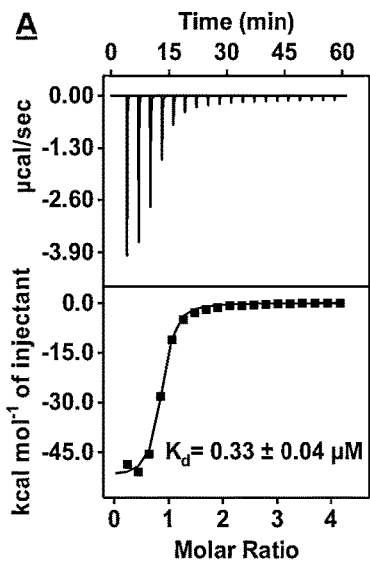
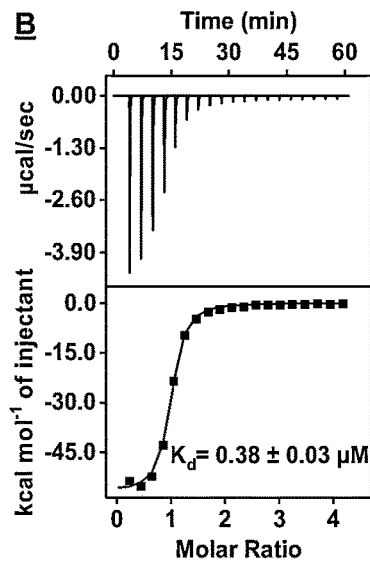
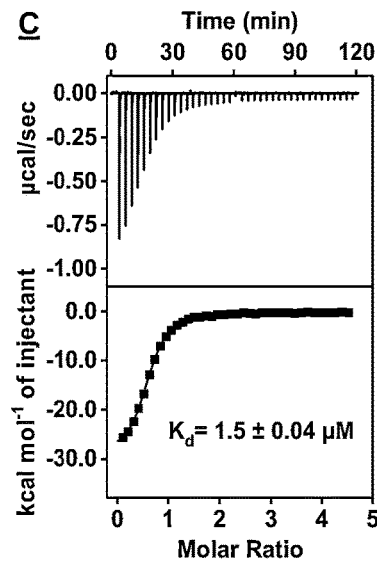
FIG. 21A                FIG. 21B                FIG. 21C
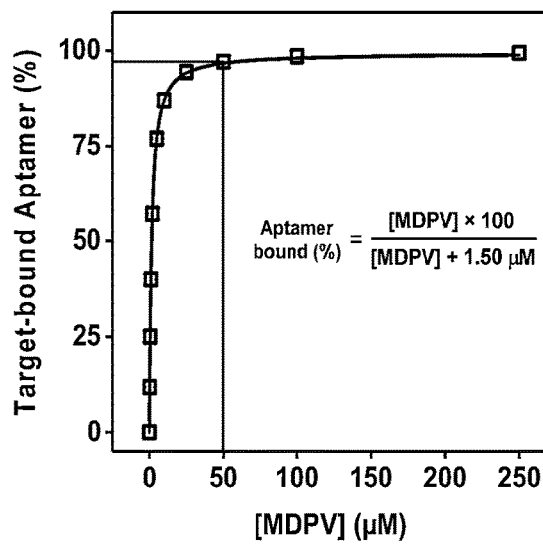
FIG. 22

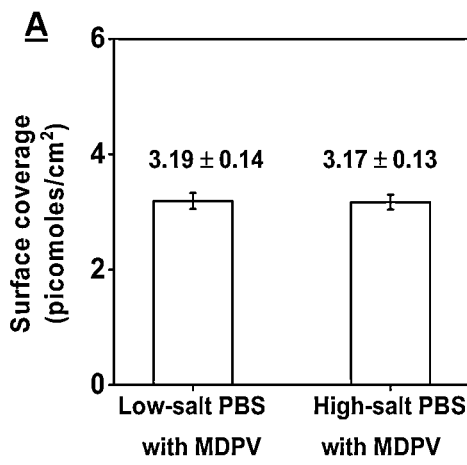
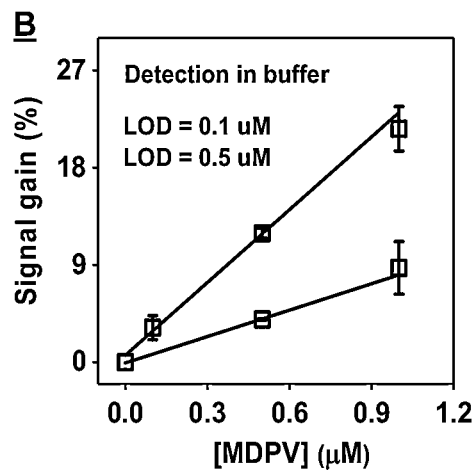
FIG. 23A
FIG. 23B
FIG. 24A
FIG. 24C
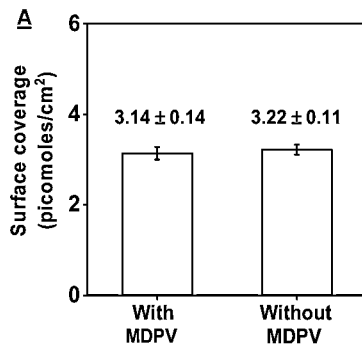
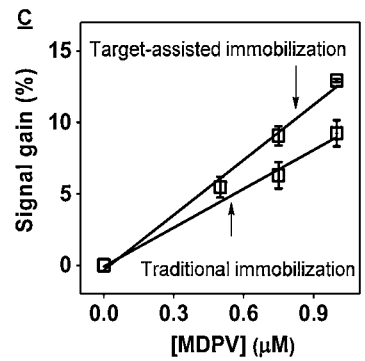
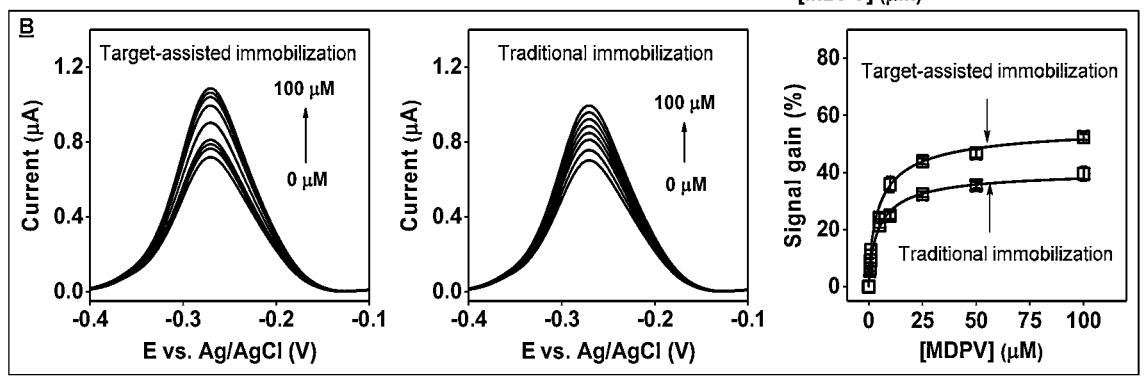
FIG. 24B

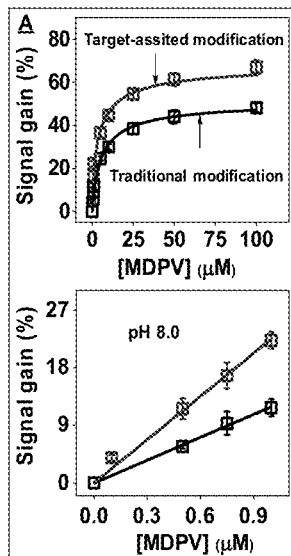 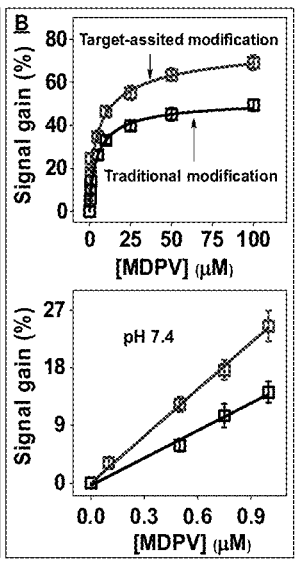 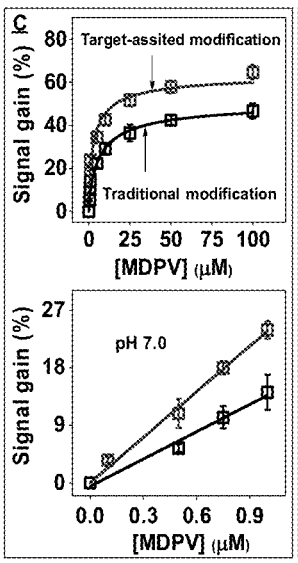 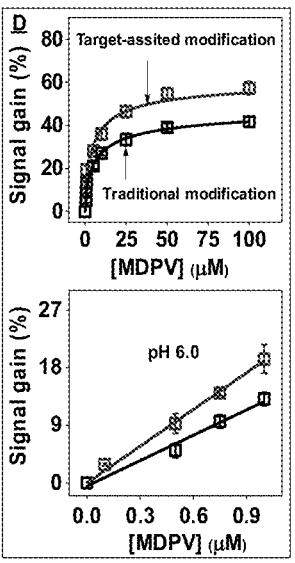
FIG. 27A    FIG. 27B    FIG. 27C    FIG. 27D
FIG. 28A
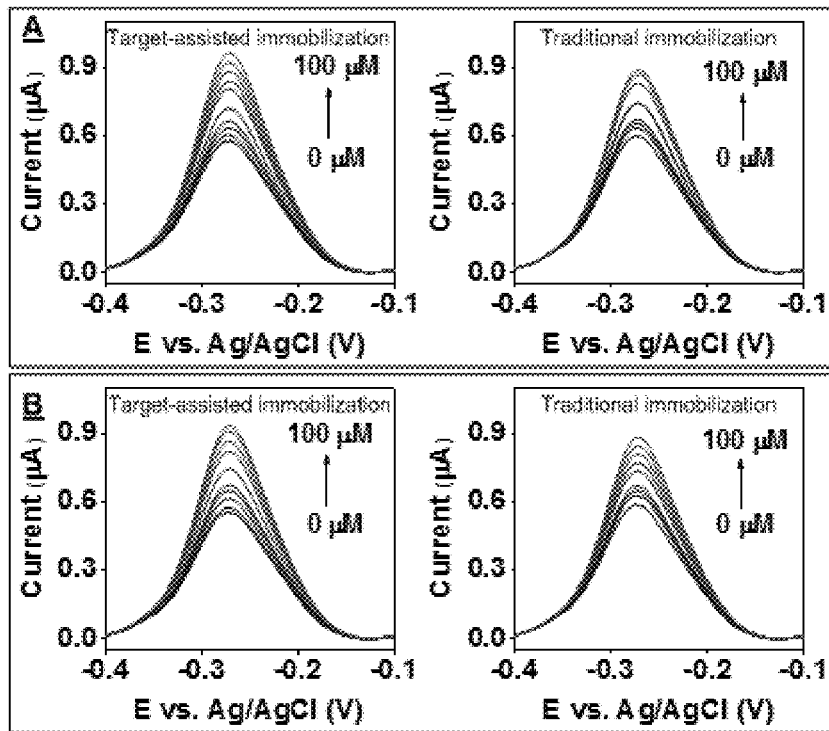
FIG. 28B FIG. 28C
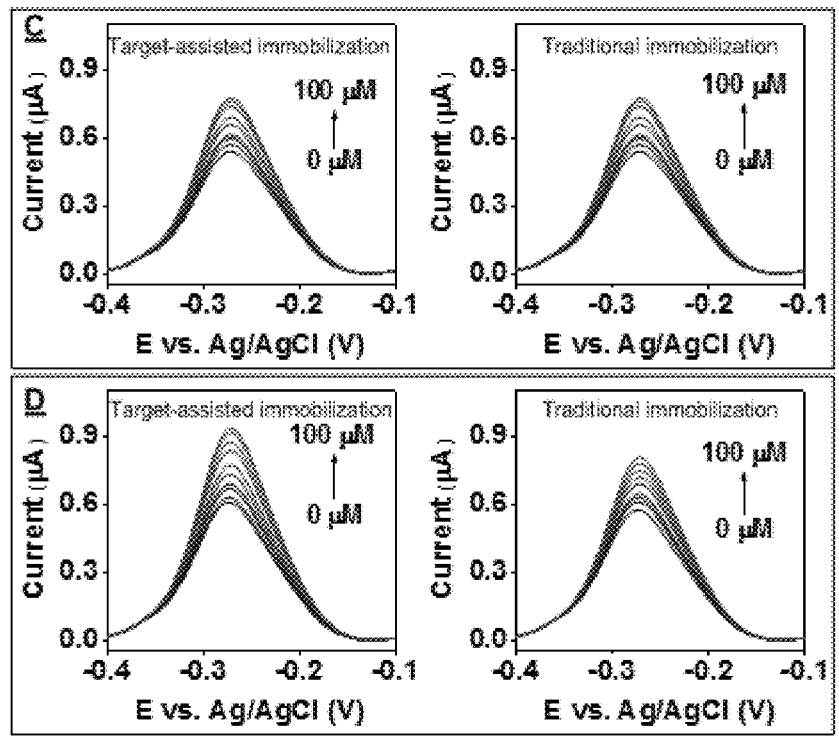
FIG. 28D
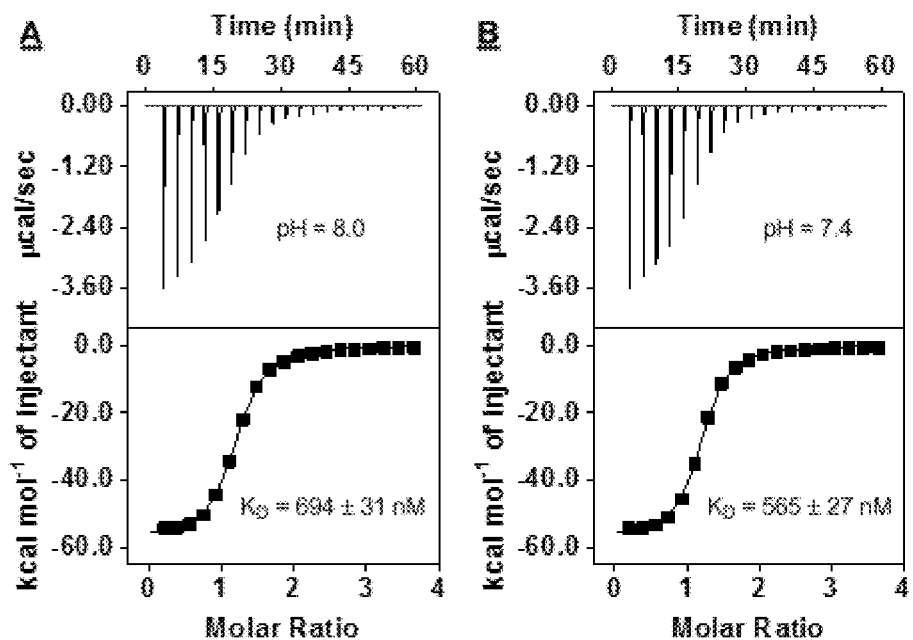
FIG. 29A  FIG. 29B

IMMOBILIZATION STRATEGIES FOR ENHANCING SENSITIVITY OF ELECTROCHEMICAL APTAMER-BASED SENSORS

CROSS-REFERENCE TO RELATED APPLICATION

This application claims the benefit of U.S. Provisional Application Ser. No. 63/288,882 filed Dec. 13, 2021, which is hereby incorporated by reference herein in its entirety.

GOVERNMENT SUPPORT

This invention was made with government support under DA045334 awarded by the National Institutes of Health and under CHM-1905143 awarded by the National Science Foundation. The government has certain rights in the invention.

SEQUENCE LISTING

The Sequence Listing for this application is labeled "SeqList-as-filed.xml," which was created on Nov. 15, 2022, and is 10,794 bytes. The entire content is incorporated herein by reference in its entirety.

BACKGROUND OF THE INVENTION

Electrochemical biosensors that utilize bioreceptors such as enzymes and antibodies can achieve rapid, sensitive, and selective detection of targets via specific molecular recognition. For example, personal glucose meters utilize the enzyme glucose oxidase to quantify glucose concentrations directly in whole blood. However, the appeal of such sensors is diminished by the lack of enzymes available for detecting a broad range of analytes, and the generally short shelf-life and high cost of protein-based bioreceptors.

Aptamers offer a promising alternative in this context; these are single-stranded DNA or RNA oligonucleotides that can be isolated from randomized libraries via an in vitro process to bind to virtually any target of interest. Aptamers can be isolated relatively quickly, have high chemical stability and long shelf-lives, and can be synthesized at low cost with minimal batch-to-batch variation.

Electrochemical aptamer-based (E-AB) sensors have great potential for diagnostic, research, and therapeutic applications because they enable rapid detection of specific analytes directly in complex samples such as soil, foodstuffs, saliva, urine, and whole blood. For example, E-AB sensors can be fabricated by immobilizing aptamers that have been modified with a terminal thiol and a redox label (usually methylene blue) onto a gold electrode via thiol-gold chemistry. This step is typically followed by backfilling with alkanethiol diluents to mitigate the adsorption of oligonucleotide probes and interferents onto the electrode surface. The aptamers employed in E-AB sensors have structure-switching functionality, meaning that they are unfolded in their unbound state and undergo a conformational change when binding to the target. This structural change alters the distance between the redox label and the electrode surface, leading to a change in current that is proportional to the concentration of the analyte.

E-AB sensors have greatly evolved in the past decade, transitioning from macroscale sensors that can only perform in vitro detection to miniaturized devices that can detect analytes directly in vivo in real time. Despite these advances, many E-AB sensors to date are incapable of detecting analytes at relevant levels for specific applications in complex samples due to their poor sensitivity and low signal-to-noise ratios. For instance, a cocaine-detecting E-AB sensor has a limit of detection (LOD) of 10 μM in blood, which is outside the range of medically- and forensically-relevant blood concentrations of cocaine (0.1-1 μM). This can be primarily attributed to the biofouling that occurs when detection is performed in biological matrices and the low target affinity of structure-switching aptamers. The biofouling problem can be remedied through the development of new monolayer chemistries and membranes that mitigate protein and cell adsorption. For example, the Plaxco group has used biomimetic zwitterionic phospholipid-based thiols as backfillers and polysulfone membranes as a physical barrier to enable continuous detection of analytes directly in the circulating blood of live animals using E-AB sensors. These strategies have significantly reduced the biofouling experienced in complex sample but has not completely eliminated it. On the other hand, the affinity issue has not been completely resolved. Although advances in aptamer selection protocols have facilitated the isolation of high-affinity aptamers, most aptamers still experience considerable reduction (10-1000 fold reduction) in binding affinity upon being engineered with structure-switching functionality via strategies, such as aptamer truncation or splitting, due to thermodynamic destabilization.

Previous reports have suggested that spacing of oligonucleotide probes on the electrode surface affects sensor performance. For example, the Fan group fabricated an E-AB sensor for cocaine by immobilizing a split cocaine-binding aptamer incorporated into a DNA tetrahedron construct tethered to the electrode surface. They hypothesized that the tetrahedron would provide the aptamer sufficient spacing to facilitate aptamer-target assembly, thereby augmenting sensor responsiveness. Indeed, they observed significant improvements in sensitivity compared to previous E-AB sensors for cocaine. Although the average spacing between aptamers can be tuned by adjusting the quantity of aptamer or buffer ionic strength employed during the immobilization step, these strategies do not allow control over the inter-oligonucleotide distance of probes at the microscopic level to favor optimal target binding and signal transduction.

Thus, there is a need to develop methods and strategies to improve the sensitivity and signal-to-noise ratio of E-AB sensors based on the spatial distribution of aptamers on the electrode surface, in particular, by controlling the inter-oligonucleotide distance at the microscopic level.

BRIEF SUMMARY OF THE INVENTION

The subject invention provides methods for fabricating electrochemical aptamer-based (E-AB) sensors with enhanced sensitivity, signal-to-noise ratios and LOD. E-AB sensors are a versatile sensing platform that can achieve rapid and robust target detection in complex matrices. The E-AB sensor of the subject invention comprises a working electrode having surface-bound aptamers sufficiently spaced to bind targets and subsequently fold for signal transduction. Advantageously, the E-AB sensors of the subject invention provide superior sensing regardless of the sequence or structure of the bound aptamers.

The subject invention also provides methods for fabricating electrodes having surface-bound aptamers sufficiently spaced to bind their targets. The electrode fabrication approach accelerates development of high-performance sensors with the sensitivity required for real-world analytical applications. The subject invention also provides a novel aptamer immobilization approach that favors sufficient spacing between aptamers at the microscale on the surface of the electrode to achieve optimal target recognition, folding, and signal transduction. This fabrication method ensures excellent stability and reproducibility of aptamer-modified electrodes. By contrast, electrodes fabricated using conventional methods result in sensing surfaces where only a fraction of aptamers are sufficiently spaced to actively respond to the target.

In one embodiment, the subject invention provides a method to improve the sensitivity and signal-to-noise ratio of E-AB sensors based on the spatial distribution of aptamers on the electrode surface. The method comprises modified aptamer immobilization steps in the electrode fabrication process, which allows control over the inter-oligonucleotide distance of probes at the microscopic level to favor optimal target binding and signal transduction and reproducibility of the sensor response. Two aspects of the modifications are 1) immobilizing aptamers in a folded, target-bound state on the electrode rather than an unbound single-stranded state as in the conventional method, and 2) lowering buffer ionic strength to reduce aptamer bundling on the surface of the electrode.

Advantageously, immobilizing the aptamer in its folded, target-bound state rather than its unfolded state, improves signal-to-noise ratio, stability, reproducibility and LOD due to optimized spacing granted by the aptamer-target complex at the microscopic level. Also, the use of low ionic strength buffers during the aptamer immobilization process mitigates the clustering of surface-bound aptamers, greatly enhancing E-AB sensing performance. These changes to the immobilization process are beneficial for E-AB sensing regardless of the aptamer sequence or structure. The methods enhance the sensitivity, stability and reproducibility of E-AB sensors for various applications.

In one embodiment, the method for fabricating the E-AB sensor comprises 1) providing an electrode, wherein the electrode is a solid or paper-based electrode which is made of, for example, gold, silver, copper, platinum, palladium, an alloy, or a mixture thereof; 2) incubating the electrode with an immobilizing solution comprising aptamer-target complexes to immobilize aptamers evenly on the surface of the electrode, wherein the immobilizing solution has a low ionic strength; 3) contacting the electrode with a solution comprising one or more backfillers, preferably, with the target, wherein the one or more backfiller are selected from 6-mercapto-1-hexanol (MCH), dithiothreitol (DTT), 9-mercapto-1-nonanol, 2-{2-[2-(2-mercaptoethoxy)ethoxy]ethoxy}ethanol and combinations thereof; and 4) removing the target.

In one embodiment, the aptamer-target complex comprises an aptamer in a folded state having its target bound to the target-binding domain, the aptamer having structure-switching functionality.

In one embodiment, the aptamer is modified with a redox tag at one end and a functional group at the other end. Preferably, the redox tag is methylene blue and the functional group is selected from, for example, thiol, sulfide, disulfide, amide, ester, alkenyl, alkynyl, carbonyl, aldehyde, carboxylate, carboxyl, and carbonate ester groups. In specific embodiments, the functional group is linked to the other end of the aptamer via a linker that comprises 1-10 carbon atoms, preferably, 2-8 carbon atoms, more preferably, 4-7 carbon atoms. In a specific embodiment, the aptamer is labeled with a thiol group at the 5' end, and methylene blue redox tag at the 3' end.

In one embodiment, the subject invention also provides a method for special distribution/immobilization of aptamers on an electrode, the method comprising incubating the electrode with an immobilizing solution comprising aptamer-target complexes; contacting the electrode with a solution comprising the target and one or more backfillers; and removing the target. In a further embodiment, the electrode is solid or a paper-based electrode which is made of gold, silver, copper, platinum, palladium, an alloy, or a mixture thereof.

In one embodiment, the subject invention further provides a method for detecting a target in a sample, the method comprising contacting the sample with the E-AB sensor of the subject invention, and detecting the target in the sample by measuring a current generated upon binding of the target to the aptamer. In a preferred embodiment, the sample is a biological sample or an environmental sample. In specific embodiments, the biological sample is selected from blood, plasma, urine, tears, sweat, and saliva.

BRIEF DESCRIPTION OF THE DRAWINGS

FIGS. 1A-1B show the characterization of the affinity of ADE-25 for adenosine using isothermal titration calorimetry (ITC). Top panels present raw data showing the heat generated from each titration of adenosine to ADE-25 in (A) low-salt Tris buffer (10 mM Tris-HCl, 20 mM NaCl, 0.5 mM $MgCl_2$, pH 7.4) or (B) high-salt PBS (1.6 mM $NaH_2PO_4$, 8.4 mM $Na_2HPO_4$, 1 M NaCl, 1 mM $MgCl_2$, pH 7.2), while bottom panels show the integrated heat of each titration after correcting for dilution heat of the titrant. ITC data were fitted with a two-site sequential binding model. $K_{1/2}=(K_{D1} \times K_{D2})^{1/2}$.

FIGS. 2A-2C show adenosine detection with electrodes modified with ADE-25-MB using the conventional immobilization approach. (A) Aptamer surface coverage of electrodes fabricated using 15 nM (A1), 25 nM (A2), or 75 nM (A3) ADE-25-MB in the absence of target. (B) Square wave voltammograms (SWV) and (C) calibration curves for adenosine detection produced by the different E-AB sensors with 0-1,000 μM adenosine. Error bars represent the standard deviation of measurements from three independently fabricated electrodes.

FIGS. 6A-6E show performance of electrodes fabricated with COC-32-MB via target-assisted immobilization or conventional means in high-salt PBS. (A) Surface coverage of electrodes fabricated by immobilizing the aptamer in the presence (w/target) or absence (w/o target) of 250 μM cocaine. SWV from electrodes fabricated via (B) target-assisted immobilization or (C) traditional means (aptamer only) and challenged with 0-1000 μM cocaine. (D) Calibration curves for detection of cocaine derived from the spectra shown in B and C. (E) Sensitivity and LOD of electrodes fabricated using target-assisted immobilization (gray) or traditional means (black). Error bars represent the standard deviation of measurements from three independently fabricated electrodes.

FIGS. 7A-7C show the characterization of the affinity of COC-32 for cocaine using ITC. Top panels present raw data showing the heat generated from each titration of cocaine to COC-32 in (A) high-salt PBS, (B) low-salt PBS, or (C) low-salt Tris buffer, while bottom panels show the integrated heat of each titration after correcting for dilution heat of the titrant. ITC data were fitted with a single-site binding model.

FIGS. 10A-10D show E-AB sensor performance using electrodes modified with COC-32-MB via target-assisted immobilization. SWV spectra collected at various concentrations of cocaine using electrodes modified in high-salt PBS with (A) 2 mM or (B) 250 μM cocaine. (C) Calibration curves derived from SWV spectra for electrodes modified with COC-32-MB plus 2 mM (brown) or 250 μM cocaine (pink) and electrodes modified with aptamer alone (black). (D) Linear ranges and LODs of electrodes fabricated via different methods. Error bars represent the standard deviation for three working electrodes from each measurement.

FIGS. 11A-11D show the performance of electrodes fabricated with COC-32-MB via conventional means in different buffers. (A) Surface coverage of electrodes fabricated by immobilizing the aptamer in high-salt or low-salt PBS. SWV produced by challenging electrodes fabricated in (B) high-salt or (C) low-salt PBS with 0-1000 μM cocaine. (D) Calibration curves for detection of cocaine derived from the spectra shown in B and C. Error bars represent the standard deviation of measurements from three independently fabricated electrodes.

FIGS. 14A-14G show the E-AB sensor performance using electrodes modified with target-bound COC-32-MB. SWV spectra at various concentrations of cocaine from electrodes modified with COC-32-MB plus cocaine in low-salt (A) PBS or (B) Tris. (C) Calibration curves derived from the SWV spectra shown in A, B, or from electrodes modified in cocaine-containing high-salt PBS. Detection of cocaine in 50% saliva using electrodes modified with (D) aptamer-target complexes in low-salt Tris or (E) aptamer alone in high-salt PBS. (F) Calibration curves derived from the SWV spectra shown in D and E. (G) Linear ranges and LODs of electrodes fabricated via different methods in buffer or 50% saliva. Error bars represent the standard deviation for three working electrodes from each measurement.

FIGS. 15A-15C show the performance of electrodes fabricated with COC-32-MB via target-assisted immobilization in different buffers. (A) Aptamer surface coverages of electrodes fabricated by immobilizing the aptamer in low-salt Tris buffer or low-salt PBS with 250 μM cocaine. SWV produced by challenging the electrodes fabricated in low-salt (B) PBS or (C) Tris buffer with 0-1000 μM cocaine. Error bars represent the standard deviation of measurements from three independently fabricated electrodes.

FIG. 16 shows the sensitivity and LOD for cocaine detection in 50% saliva with electrodes fabricated using COC-32-MB via target-assisted immobilization in low-salt Tris buffer with 250 μM cocaine (gray) or conventional means in high-salt PBS (black). Error bars represent the standard deviation of measurements from three independently fabricated electrodes.

FIG. 17 shows the simulated binding curve for SC-34 based on affinity for MDPV in low-salt Tris buffer ($K_D$=0.33 μM, for (–)–MDPV). The blue lines indicate that 94%, 97%, and 99% of the aptamer is bound in the presence of 5, 10, and 50 μM MDPV, respectively.

FIGS. 18A-18G show the E-AB sensor performance using electrodes fabricated with SC-34-MB. (A) Effect of MDPV concentration on surface coverage during electrode modification. (B) Signal gain for the various electrodes prepared in A from various concentrations of MDPV in buffer. (C) Detection of MDPV in 50% urine using modified electrodes prepared in low-salt Tris with SC-34-MB alone (M1) or in the presence of 50 μM MDPV (M4). SWV spectra from various concentrations of MDPV using electrodes modified via target-assisted immobilization in either (D) low-salt or (E) high-salt PBS. (F) Calibration curves derived from the SWV spectra shown in D and E or from electrodes prepared in low-salt or high-salt Tris buffer. (G) Linear ranges and LODs of electrodes fabricated via different methods in buffer or 50% urine. Error bars represent the standard deviation for three working electrodes from each measurement.

FIGS. 21A-21C show the characterization of the affinity of SC-34 for (–)–MDPV using ITC. Top panels present raw data showing the heat generated from each titration of (–)–MDPV to SC-34 in (A) low-salt Tris buffer, (B) low-salt PBS, or (C) high-salt PBS, while bottom panels show the integrated heat of each titration after correcting for dilution heat of the titrant. ITC data were fitted with a single-site binding model.

FIG. 22 shows the simulated binding curve for SC-34 based on affinity for MDPV in high-salt PBS ($K_D$=1.50 μM, for (−)−MDPV). The blue lines indicate that 97% of the aptamer is bound in the presence of 50 μM MDPV.

FIGS. 23A-23B show the performance of electrodes fabricated with SC-34-MB via target-assisted immobilization in different buffers. (A) Surface coverage of electrodes fabricated by immobilizing the aptamer in low-salt or high-salt PBS with 50 μM MDPV. (B) Calibration curve and LOD for MDPV detection using electrodes modified with SC-34-MB via target-assisted immobilization in low-salt (gray) or high-salt PBS (black). Error bars represent the standard deviation of measurements from three independently fabricated electrodes.

FIGS. 24A-24C show the performance of electrodes fabricated with SC-34-MB in the presence or absence of 50 μM MDPV in high-salt Tris buffer. (A) Aptamer surface coverage of fabricated electrodes. (B) SWV measurements from electrodes fabricated via target-assisted aptamer immobilization approach (left) or traditional aptamer immobilization (middle) in the presence of 0-100 μM MDPV. The derived calibration curve is shown at right. (C) Linear ranges from the curves shown in B. Error bars represent the standard deviation of measurements from three independently fabricated electrodes.

FIGS. 27A-27D show the E-AB sensor performance using electrodes modified with SC-34-MB in the presence (target-assisted immobilization) or absence (traditional immobilization) of 50 μM MDPV in low-salt PBS at pH (A) 8.0, (B) 7.4, (C) 7.0 and (D) 6.0. The top panels show calibration curves for electrodes fabricated via target-assisted aptamer immobilization (gray) or traditional modification method (black) produced by challenging with 0-100 μM MDPV, and bottom panels show their respective linear ranges. Error bars represent the standard deviation of measurements from three independently fabricated electrodes.

FIGS. 28A-28D show the SWV of E-AB sensor using electrodes modified with SC-34-MB in the presence (target-assisted immobilization) or absence (traditional immobilization) of 50 μM MDPV in low-salt PBS at pH (A) 8.0, (B) 7.4, (C) 7.0 and (D) 6.0. SWV spectra for electrodes prepared under these two immobilization conditions and then exposed to 0-100 μM MDPV. Error bars represent the standard deviation of measurements from three independently fabricated electrodes.

FIGS. 29A-29D show the characterization of the pH-dependence of SC-34 affinity for MDPV using ITC. Top panels present raw data showing the heat generated from each titration of MDPV to SC-34 in low-salt PBS at pH (A) 8.0, (B) 7.4, (C) 7.0, or (D) 6.0, while bottom panels show the integrated heat of each titration after correcting for dilution heat of the titrant. ITC data were fitted with a single-site binding model.

BRIEF DESCRIPTION OF THE SEQUENCES

Figure 3:
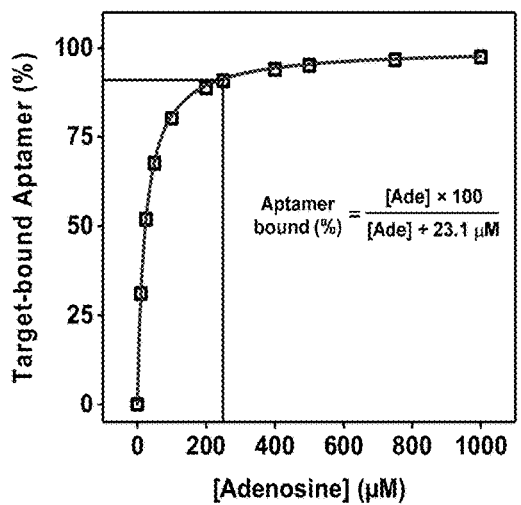
FIG. 3 shows the simulated binding curve for ADE-25 based on its affinity for adenosine in high-salt PBS ($K_{1/2}=23.1$ μM). Blue lines indicate that ~91% of the aptamer is bound in the presence of 250 μM adenosine.

SEQ ID NO: 1 is a sequence of an adenosine-binding DNA aptamer contemplated for use according to the subject invention.

SEQ ID NO: 2 is a sequence of a cocaine-binding DNA aptamer contemplated for use according to the subject invention.

SEQ ID NO: 3 is a sequence of a 3',4'-methylenedioxy-pyrovalerone (MDPV)-binding DNA aptamer contemplated for use according to the subject invention.

SEQ ID NO: 4 is a sequence of a modified adenosine-binding DNA aptamer contemplated for use according to the subject invention.

SEQ ID NO: 5 is a sequence of a modified cocaine-binding DNA aptamer contemplated for use according to the subject invention.

SEQ ID NO: 6 is a sequence of a modified MDPV-binding DNA aptamer contemplated for use according to the subject invention.

DETAILED DESCRIPTION OF THE INVENTION

The subject invention provides electrochemical aptamer-based (E-AB) sensors with enhanced sensitivity, signal-to-noise ratios, limit of detection (LOD), stability, and reproducibility and methods for fabricating such E-AB sensors. E-AB sensors are a versatile sensing platform that can achieve rapid and robust target detection in complex matrices. In one embodiment, the E-AB sensor comprises a working electrode having surface-bound aptamers sufficiently spaced at the microscopic level to bind targets and subsequently folding with optimal space for signal transduction. Advantageously, the E-AB sensors of the subject invention provide superior sensing regardless of the sequence or structure of the bound aptamers.

In preferred embodiments, aptamers bound on the surface of the electrode are sufficiently spaced at the microscopic level such that aptamers are immobilized on the surface with the distance between aptamers and sufficient for target binding to each aptamer and subsequently change in aptamer conformation from an unfolded state to a target-bound folded state. Sufficient spacing of the aptamers at the microscopic level on the surface of the electrode avoids the formation of aptamer clusters that prevents target binding to the aptamers and the subsequent conformational change.

In one embodiment, the subject invention provides an electrode fabrication approach that accelerates development of high-performance sensors with the sensitivity required for real-world analytical applications. The subject invention also provides a novel aptamer immobilization approach that utilizes sufficient spacing between aptamers at the microscale on the surface of the electrode to achieve improved target recognition, folding, and signal transduction. By contrast, electrodes fabricated using conventional methods result in sensing surfaces where only a fraction of the aptamers are sufficiently spaced to actively respond to the target.

In one embodiment, the subject invention provides a method to improve the sensitivity and signal-to-noise ratio of E-AB sensors based on the spatial distribution of aptamers on the electrode surface. The method comprises modified aptamer immobilization steps in the electrode fabrication process, which allows control over the inter-oligonucleotide distance of probes at the microscopic level to achieve improved target binding and signal transduction.

In one embodiment, the subject invention provides two aspects of the electrode modification step that one used to improve spacing of surface-bound aptamer probes. The two aspects of the modifications are 1) immobilizing aptamers in a folded, target-bound state on the electrode rather than an unbound single-stranded state as in the conventional method, and 2) lowering buffer ionic strength to reduce aptamer bundling on the surface of electrode.

Advantageously, immobilizing the aptamer in its folded, target-bound state rather than its unfolded state, as is done conventionally, improves signal-to-noise ratio, stability, reproducibility and LOD due to optimized spacing granted by the aptamer-target complex at the microscopic level. Also, the use of low ionic strength buffers during the aptamer immobilization process greatly enhances E-AB sensing performance. This improvement in performance can be attributed to mitigation of the clustering of surface-bound aptamers, which commonly occurs when high ionic strength buffers are utilized in conventional protocols. These changes to the immobilization process are beneficial for E-AB sensing regardless of the aptamer sequence or structure. The enhanced immobilization protocols are highly valuable for the reproducible fabrication of E-AB sensors with greater sensitivity and stability.

In one embodiment, the method for fabricating an E-AB sensor comprises providing an electrode; incubating/contacting the electrode with a solution comprising aptamer-target complexes to immobilize aptamers in a target-bound, folded state on the electrode surface; incubating/contacting the electrode with a solution comprising the target and one or more backfillers to fill the vacant areas on the electrode surface; and removing the target from the aptamer-target complexes.

In one embodiment, the method for fabricating an aptamer-modified electrode of an E-AB sensor comprises incubating/contacting the electrode with a solution comprising aptamer-target complexes to immobilize aptamers in a target-bound, folded state on the electrode surface; incubating/contacting the electrode with a solution of the target and one or more backfillers to fill the vacant areas on the electrode surface; and removing the target to obtain the aptamer-modified electrode, wherein the aptamer-modified electrode having surface-bound aptamers sufficiently spaced on the surface of the electrode and the aptamers are in an unfolded state.

Advantageously, immobilizing aptamers in their target-bound, folded state on electrode surface yields an aptamer monolayer that provides greater sensitivity, stability, reproducibility, and higher signal-to-noise ratio than traditionally-prepared E-AB sensors. In preferred embodiments, the aptamer-modified electrode does not comprise aptamer clusters or bundles on the surface of the electrode.

In one embodiment, the subject invention provides a method for evenly or spatial immobilizing aptamers on the surface of an electrode, the method comprising incubating/contacting the electrode with a solution comprising aptamer-target complexes to immobilize aptamers in a target-bound, folded state on the electrode surface; incubating/contacting the electrode with a solution of the target and one or more backfillers; and removing the target.

In one embodiment, the subject invention provides a method for even or spatial distribution of aptamers on the surface of an electrode, the method comprising incubating/contacting the electrode with a solution comprising aptamer-target complexes to immobilize aptamers in a target-bound, folded state on the electrode surface; incubating/contacting the electrode with a solution of the target and one or more backfillers; and removing the target.

The electrode can be, for example, any type of paper-based electrode or metal electrode which is made from, for example, gold, silver, copper, platinum, palladium, an alloy, and mixtures thereof. The electrode may have any shape suitable for the E-AB sensor. Exemplary shapes of electrode include, but are not limited to, wire, rod, sheet, plate, and disc. In one embodiment, the electrode may have a size ranging from, for example, about 100 nm to about 50 mm, from about 500 nm to about 10 mm, or from about 1 mm to about 5 mm. In a specific embodiment, the electrode has a diameter about 1, 2 or 3 mm.

In one embodiment, the aptamer for modifying the electrode has structure-switching functionality that allows the aptamer to undergo target-induced conformational changes. In the absence of the target, the aptamer exists in an unfolded single-stranded state while in the presence of the target, the aptamer folds into an aptamer-target complex with the target bound in the binding domain. Aptamers having structure-switching functionality have been disclosed in, for example, U.S. Pat. Nos. 11,162,960, and 10,655,132, which are incorporated herein by reference in their entirety.

Aptamers are nucleic acid molecules characterized by the ability to bind to a target molecule with high specificity and high affinity. Almost every aptamer identified to date is a non-naturally occurring molecule. Aptamers to a given target may be identified and/or produced by the method of systematic evolution of ligands by exponential enrichment (SELEX).

In one embodiment, the aptamer is an oligonucleotide, such as DNA or RNA molecules and may be single-stranded or double-stranded. In a preferred embodiment, the aptamer is a DNA aptamer.

The aptamer may be partially or fully folded to form various secondary structures (e.g., stems, loops, bulges, pseudoknots, G-quadruplexes and kissing hairpins), which in turn can form unique three-dimensional architectures able to specifically recognize their targets by exploiting a variety of interactions—such as hydrophobic and electrostatic interactions, hydrogen bonding, van der Waals forces, and $\pi$-$\pi$ stacking as well as shape complementarity. The aptamer used in the subject invention may have any structure, e.g., hairpin structure, three-way junction (TWJ) structure or a combination thereof.

As used herein, the terms "polynucleotide," "nucleotide," "oligonucleotide," and "nucleic acid" refer to a nucleic acid comprising DNA, RNA, derivatives thereof, or combinations thereof.

In one embodiment, the aptamer according to the present invention may comprise at least 10, at least 20, at least 30, at least 40, at least 50, at least 60, at least 70, or at least 80 nucleotides. The aptamer according to the present invention, preferably, comprises 10 to 200 nucleotides, preferably 15 to 150 nucleotides, more preferably 20 to 100 nucleotides, most preferably, 30 to 60 nucleotides.

In one embodiment, the aptamer according to the present invention has a minimum length of, for example, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 nucleotides. The aptamer according to the present invention may have a maximum length of, for example, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, or 150 nucleotides. The aptamer according to the present invention may have a length of, for example, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 nucleotides.

The aptamers of the present invention may or may not include chemical modifications. The chemical modifications as described herein include a chemical substitution at a sugar position, a phosphate position, and/or a base position of the nucleic acid including, for example, incorporation of a modified nucleotide, incorporation of a capping moiety (e.g., 3' capping), conjugation to a high molecular weight, non-immunogenic compound (e.g., polyethylene glycol (PEG)), conjugation to a lipophilic compound, and substitutions in the phosphate backbone. Base modifications may include 5-position pyrimidine modifications, modifications at exocyclic amines, substitution of 4-thiouridine, substitution of 5-bromo- or 5-iodo-uracil, and backbone modifications. Sugar modifications may include 2'-amine nucleotides (2'-NH2). 2'-fluoronucleotides (2'-F), and 2'-O-methyl (2'-OMe) nucleotides. Such modifications may improve the stability of the aptamers or make the aptamers more resistant to degradation. In some embodiments, each base of a given type (e.g., A, T, C, and G) may contain the same chemical modification.

The aptamers may or may not be modified by addition of one or more reporter labels (or detectable labels). In some embodiments, the label may be attached to the 5' and/or 3' end of the aptamer. The label may also be attached within the backbone of the aptamer. The skilled person will be aware of techniques for attaching labels to nucleic acid strands. The detectable label may be attached directly or indirectly to the nucleic acid aptamer. If the label is indirectly attached to the nucleic acid aptamer, it may be by any mechanism known to one of skill in the art, such as using biotin and streptavidin.

The aptamers may or may not comprise a detectable label, such as a fluorescent dye, nanoparticle, or an enzyme. Exemplary labels include, but are not limited to, an organic donor fluorophore or an organic acceptor fluorophore, a luminescent lanthanide, a fluorescent or luminescent nanoparticle, an affinity tag such as biotin, or a polypeptide. In some embodiments, the aptamer may comprise a fluorescent label, for example, fluorescein, TAMRA™, rhodamine, TEXAS RED™, ALEXA FLUOR™(e.g., ALEXA FLUOR® 488, ALEXA FLUOR® 532, ALEXA FLUOR® 546, ALEXA FLUOR® 594, ALEXA FLUOR® 633 and ALEXA FLUOR® 647), cyanine dye (e.g., CY7™, CY7.5™, CY5™, CY5.5™ and CY3™), TYE™ dye (e.g., TYE™ 563, TYE™ 665, and TYE™ 705), ATTO™ dye (e.g., ATTO™ 594 and ATTO™ 633), Hexachlorofluorescein, FAM (6-carboxyfluroescein), BODIPY FL, OliGreen, 40,6-diamidino-2-phenylindol (DAPI), Hoechst 33,258, malachite green (MG), and FITC. The nanoparticle can be a gold nanoparticle or an upconversion nanoparticle. In some embodiments, the fluorophore is selected from the group consisting of fluorophores that emit a blue, green, near red or far red fluorescence.

In one embodiment, the reporter label can be an electroactive molecule, for example, methylene blue, ferrocene, or an enzyme that can convert nonelectroactive substrates into electroactive products.

In one embodiment, the structure-switching aptamer comprises modifications at 5' and 3' ends. In a specific embodiment, the structure-switching aptamer comprises a redox tag at one end and a functional group at the other end, wherein the structure-switching aptamer is conjugated to the surface of the electrode via the functional group. In one embodiment, the functional groups include, but are not limited to, thiol, sulfide, disulfide, amide, ester, alkenyl, alkynyl, carbonyl, aldehyde, carboxylate, carboxyl, and carbonate ester groups.

In the absence of a target, the structure-switching aptamer is primarily unfolded, prohibiting electron transfer from the redox tag to the electrode. In the presence of a target, the structure-switching aptamer undergoes a target-induced conformational change that brings the redox tag close to the electrode surface, facilitating efficient electron transfer and resulting in an increase in current within seconds.

In a preferred embodiment, the functional group is thiol at the 5' or 3' end, and the redox tag is a methylene blue (MB) redox tag at the 3' or 5' end. In a specific embodiment, the aptamer is modified with a 5' thiol and a 3' methylene blue redox tag. The thiol group may be linked to the 5' end of the aptamer via a first linker and the methylene blue redox tag may be linked to the 3' end of the aptamer via a second linker. The first and second linkers may be different or identical. Each of the first and second linkers independently comprises 1-10 carbon atoms, e.g., C1-C10 alkylene. Preferably, each of the first and second linkers independently comprises 2-8 carbon atoms. More preferably, the first linker is a 6-carbon linker (i.e., $-(CH_2)_6-$) and the second linker is a 7-carbon linker (i.e., $-(CH_2)_7-$).

In certain embodiments, the aptamer is immobilized on the electrode of the E-AB sensor at a density ranging from about 1 to about 12 picomoles/cm$^2$, about 1.2 to about 11 picomoles/cm$^2$, about 1.5 to about 10 picomoles/cm$^2$, about 1.5 to about 9 picomoles/cm$^2$, about 1.5 to about 8 picomoles/cm$^2$, about 1.5 to about, 7 picomoles/cm$^2$, about 1.5 to about 6 picomoles/cm$^2$, about 1.5 to about 5 picomoles/cm$^2$, about 1.5 to about 4.5 picomoles/cm$^2$, about 1.5 to about 4 picomoles/cm$^2$, or about 1.89 to about 3.77 picomoles/cm$^2$.

In one embodiment, the solution comprising aptamer-target complexes comprises the target at a concentration of, for example, from about 5 µM to about 10 mM, from about 10 µM to about 10 mM, from about 50 µM to about 10 mM, from about 100 µM to about 5 mM, from about 150 µM to about 4.5 mM, from about 200 µM to about 4 mM, from about 250 µM to about 3.5 mM, from about 300 µM to about 3 mM, from about 350 µM to about 2.5 mM, from about 400 µM to about 2 mM, from about 500 µM to about 2 mM, from about 500 µM to about 5 mM, from about 1 mM to about 5 mM, from about 1 mM to about 4 mM, from about 1 mM to about 3 mM, from about 1 mM to about 2 mM, or from about 5 µM to about 100 µM. In one embodiment, the solution of aptamer-target complexes comprises the target at a concentration of at least 1 µM, 5 µM, 10 µM, 50 µM, 100 µM, 200 µM, 500 µM, 1 mM, 2 mM, or 3 mM.

In one embodiment, the solution comprising aptamer-target complexes is a low salt solution having a total salt concentration, for example, from about 1 mM to about 200 mM, from about 5 mM to about 200 mM, from about 5 mM to about 175 mM, from about 10 mM to about 150 mM, from about 10 mM to about 120 mM, from about 10 mM to about 100 mM, from about 10 mM to about 90 mM, from about 10 mM to about 80 mM, from about 10 mM to about 70 mM, from about 10 mM to about 60 mM, from about 10 mM to about 50 mM, from about 10 mM to about 40 mM, from about 10 mM to about 30 mM, from about 10 mM to about 20 mM, or from about 1 mM to about 20 mM.

In one embodiment, the solution of aptamer-target complexes has an ionic strength of, for example, at least 1 mM, 5 mM, 10 mM, 15 mM, 20 mM, 25 mM, 30 mM, 35 mM, 40 mM, 45 mM, 50 mM, 55 mM, 60 mM, 65 mM, 70 mM, 80 mM, 90 mM, 100 mM, 110 mM, 120 mM, 130 mM, 140 mM, 150 mM, 160 mM, 170 mM, 180 mM, 190 mM, 200 mM or any value therebetween. In one embodiment, the solution of aptamer-target complexes has an ionic strength, for example, from about 0.5 mM to about 1 M, from about 1 mM to about 1 M, from about 2 mM to about 900 mM, from about 5 mM to about 800 mM, from about 10 mM to about 700 mM, from about 10 mM to about 600 mM, from about 10 mM to about 500 mM, from about 10 mM to about 400 mM, from about 10 mM to about 300 mM, from about 10 mM to about 200 mM, from about 10 mM to about 100 mM, or from about 10 mM to about 50 mM.

In one embodiment, the solution of aptamer-target complexes comprises at least one cation, for example, $Mg^{2+}$ and/or $Na^+$. The salt may be, for example, $MgCl_2$ and/or NaCl. The salt may be used at the physiological concentration or any concentrations suitable for immobilizing the aptamers on the surface of the electrode with sufficient spacing.

Exemplary concentrations of magnesium salt may be between about 0 mM and about 50 mM, between about 0.1 mM and about 40 mM, between about 0.2 mM and about 30 mM, between about 0.5 mM and about 20 mM, between about 1 mM and about 15 mM, between bout 2 mM and about 10 mM, between about 3 mM and about 8 mM, between about 0 mM and about 5 mM, between about 0 mM and about 2 mM, between about 0 mM and about 1 mM, between about 0.01 mM and about 0.5 mM, or between about 0.02 mM and about 0.1 mM.

Exemplary concentrations of sodium salt may be between about 0 mM and about 1 M, between about 0 mM and about 500 mM, between about 0 mM and about 200 mM, between about 0 mM and about 100 mM, between about 0 mM and about 50 mM, between about 0 mM and about 40 mM, between about 0 mM and about 30 mM, between about 0 mM and about 20 mM, between about 0 mM and about 15 mM, between about 0 mM and about 10 mM, between about 0 mM and about 5 mM, between about 0 mM and about 1 mM, between about 0.05 mM and about 1 mM, or between about 0.1 mM and about 0.5 mM, In one embodiment, the solution of aptamer-target complexes has a pH value of 6-9, 7-9, or 7-8.

In one embodiment, the backfiller filling vacant areas on the electrode surface includes 6-mercapto-1-hexanol (MCH), dithiothreitol (DTT), 9-mercapto-1-nonanol, 2-{2-[2-(2-mercaptoethoxy)ethoxy]ethoxy}ethanol, and/or a combination thereof The backfiller may be modified or unmodified. In a specific embodiment, the backfiller is immobilized on the surface of the electrode, for example, via thiol-gold chemistry.

In certain embodiments, the backfiller may be used at concentrations between about 10 µM to about 50 mM, from about 100 µM to about 40 mM, from about 200 µM to about 30 mM, from about 500 µM to about 20 mM, from about 1 mM to about 10 mM, from about 2 mM to about 9 mM, and from about 2 mM to about 5 mM. In a preferred embodiment, the backfiller is used, either alone or in combination, at a concentration of 1 mM, 2 mM, 3 mM, 4 mM, or 5 mM.

In one embodiment, the subject invention provides a method for controlling microscale probe spacing on a substrate, the method comprising incubating/contacting the substrate with a solution of one or more probes. In one embodiment, the substrate is an electrode. In one embodiment, the method further comprises incubating/contacting the substrate with a solution of the target and one or more backfillers. In one embodiment, the probe is an aptamer or aptamer-target complex.

In one embodiment, the subject invention provides an E-AB sensor fabricated according to the method of the subject invention. The E-AB sensor comprises an electrode surface modified with aptamers labeled with a redox tag at one end and a functional group on the other end, wherein the aptamers are immobilized on the electrode surface via the functional group and are sufficiently spaced on the electrode surface to maximize the target binding. Preferably, the functional group is thiol, and the redox tag is a methylene blue (MB) redox tag, which may label the aptamer at the 5' end, 3' end, or within the backbone. In a preferred embodiment, the electrode is made of, for example, gold, silver, or platinum.

In one embodiment, the E-AB sensor further comprises a reference electrode, e.g., an Ag/AgCl reference electrode, and a counter electrode, e.g., a platinum counter electrode.

In a preferred embodiment, the aptamer is labeled with a 5' thiol and a 3' methylene blue (MB) redox tag and the modified aptamer is immobilized on a gold electrode surface via thiol-gold chemistry. In specific embodiments, the aptamer has structure-switching functionality that enables the aptamer a large conformational change upon binding of the target to form an aptamer-target complex.

In some embodiments, at least 50%, 55%, 60%, 65%, 70%, 75%, 80%, 85%, 90%, 95%, 98%, 99%, or 99.9% of the aptamers immobilized on the surface of the electrode are active aptamers that can bind targets. The inactive aptamers refer to those that are in dense clusters and cannot bind targets.

The subject invention further provides methods of using the E-AB sensors of the subject invention for detecting a target molecule in a complex sample, in particular, in both clinical and field settings. In one embodiment, the method comprises providing a sample, contacting the sample with the E-AB sensor, and detecting the target in the sample.

In one embodiment, the detection of the target comprises measuring a signal generated upon contacting the sample with the aptamer modified electrode of the E-AB sensor, wherein the signal is a change in current. In the absence of a target, the structure-switching aptamer immobilized on the surface of the electrode is primarily unfolded, prohibiting electron transfer from the redox tag to the electrode. In the presence of a target, the structure-switching aptamer undergoes a target-induced conformational change that brings the redox tag close to the electrode surface, facilitating efficient electron transfer and resulting in an increase in current within seconds.

In another embodiment, the method further comprises determining the concentration of the target molecule in the sample. The determination comprises comparing the current generated upon binding of the target with the aptamer immobilized on the surface of the electrode with a standard curve. The read-out can be quantified in seconds by, for example, a potentiostat. Thus, the current measured upon binding of the target with the surface-bound aptamer is indicative of the presence of the target in such sample.

In one embodiment, the sample is a biological sample of a subject. In specific embodiments, the biological sample is selected from blood, plasma, urine, tears, sweat, and saliva. The subject may be any animal or human, preferably, a human. The subject may also be any animal including, but not limited to, non-human primates, rodents, dogs, cats, horses, cattle, pigs, sheep, goats, chickens, guinea pigs, hamsters and the like.

In one embodiment, the sample is an environmental sample, for example, water, soil, air, or plant sample. In another embodiment, the sample is a seized drug sample, for instance, a plant material sample, or a street drug sample seized by law enforcement or government officials.

In one embodiment, the method according to the subject invention can achieve superior sensitivity for target detection at low micromolar or nanomolar concentration, for example, as low as about 10 µM, about 5 µM, about 2 µM, about 1 µM, about 100 nM, or about 10 nM. Advantageously, the LOD of the E-AB sensor comprising the aptamer-modified electrode fabricated according to the subject invention is at least 5%, 10%, 15%, 20%, 25%, 30%, 35%, 40%, 45%, 50%, 55%, 60%, 65%, 70%, 75% better or lower than that of the E-AB sensor fabricated using the conventional approach.

In one embodiment, the methods for detecting a target provided herein are rapid and can be completed in, for example, about 5 seconds to about 60 minutes, about 10 seconds to about 50 minutes, about 10 seconds to about 40 minutes, about 10 seconds to about 30 minutes, about 10 seconds to about 20 minutes, about 10 seconds to about 15 minutes, about 10 seconds to about 10 minutes, about 10 seconds to about 5 minutes, about 10 seconds to about 4 minutes, about 15 seconds to about 3 minutes, about 20 seconds to about 2 minutes, or about 25 seconds to about 1 minute.

The term "target" used herein extends to any molecule capable of being detected using an aptamer technique. In specific embodiments, the target may be an amino acid, an amino acid-related molecule, a peptide, a steroid, a lipid, a sugar, a carbohydrate, a biomarker, a drug molecule, a drug metabolite, a coenzyme, a nucleotide (nt), a nucleotide-related molecule, a pyridine nucleotide, a cyclic nucleotide, or a cyclic dinucleotide. In another embodiment, the target may be an infective agent, antigen, toxin, disease biomarker and/or specific metal ion.

In certain embodiments, the target according to the subject invention is a drug molecule, including cannabinoids such as natural cannabinoids, synthetic cannabinoids, cannabinoid derivatives and cannabimimetics. Cannabinoids include, but are not limited to, tetrahydrocannabinol (THC), tetrahydrocannabinolic acid (THCA), cannabidiol (CBD), cannabidiolic acid (CBDA), cannabinol (CBN), cannabigerol (CBG), cannabichromene (CBC), cannabicyclol (CBL), cannabivarin (CBV), tetrahydrocannabivarin (THCV), cannabidivarin (CBDV), cannabichromevarin (CBCV), cannabigerovarin (CBGV), cannabigerol monomethyl ether (CBGM), cannabielsoin (CBE), cannabicitran (CBT), arachidonoylethanolamine (Anandamide or AEA), 2-arachidonoylglycerol (2-AG), 2-arachidonyl glyceryl ether, N-arachidonoyl dopamine (NADA), virodhamine (OAE), lysophosphatidylinositol (LPI), naphthoylindoles, naphthylmethylindoles, naphthoylpyrroles, naphthylmethylindenes, phenylacetylindoles, adamantoylindoles, cyclohexylphenols, tetramethylcyclopropylindoles, indazole carboxamides, and quinolinyl ester.

In certain embodiments, the target molecule according to the subject invention is selected from the fentanyl family, including fentanyl, its analogs, its derivatives and salts thereof. In a specific embodiments, the target molecules are fentanyl-related molecules that includes, but are not limited to, fentanyl, acetyl fentanyl, furanyl fentanyl, acrylfentanyl, butyryl fentanyl, valeryl fentanyl, cyclopropyl fentanyl, methoxyacetyl fentanyl, cis-3-methyl fentanyl, p-methoxy furanyl fentanyl, p-fluoro fentanyl, p-methoxy butyryl fentanyl, remifentanil, alpha-methyl thiofentanyl, o-methyl furanyl fentanyl, and p-fluoroisobutyryl fentanyl.

In one embodiment, the target molecule is a drug molecule. In specific embodiments, the drug molecule is cocaine or a cocaine derivative. The cocaine derivative may or may not have the core structure of cocaine. Exemplary cocaine derivatives include, but are not limited to, 4-fluorococaine, 2-hydroxycocaine, 3-(p-fluorobenzoyloxy)tropane (pFBT), procaine, and dimethocaine.

In one embodiment, the target molecule comprises a nucleobase, such as adenine (A), cytosine (C), guanine (G), thymine (T), and uracil (U). The target molecule may also comprise a nucleoside including ribonucleoside and deoxyribonucleoside. Examples include, but are not limited to, adenosine triphosphate (ATP), adenosine diphosphate (ADP), adenosine monophosphate (AMP), cyclic adenosine monophosphate (cAMP), guanosine triphosphate (GTP), guanosine diphosphate (GDP), guanosine monophosphate (GMP), and cyclic guanosine monophosphate (cGMP).

The "salts" can be with an inorganic acid, such as hydrochloric acid, hydrobromic acid, perchloric acid, nitric acid, thiocyanic acid, sulfuric acid, and phosphoric acid; an organic acid, such as citric acid, trifluoroacetic acid (TFA), formic acid, acetic acid, propionic acid, glycolic acid, lactic acid, pyruvic acid, oxalic acid, malonic acid, succinic acid, maleic acid, and fumaric acid; or a salt with a base, such as sodium hydroxide, ammonium hydroxide, potassium hydroxide, and organic bases.

In one embodiment, the target molecules are cathinones or synthetic cathinones, which include, but are not limited to, 3', 4'-methylenedioxypyrovalerone (MDPV); 4'-methyl-α-pyrrolidinohexanophenone (MPHP); naphyrone; methylone; ethylone; butylone; pentylone; mephedrone; mexedrone; buphedrone; pentedrone; hexedrone; heptedrone; α-pyrrolidinopropiophenone (α-PPP); 4'-methyl-α-pyrrolidinopropiophenone (M-α-PPP); 3',4'-methylenedioxy-α-pyrrolidinopropiophenone (MDPPP); 1-phenyl-2-(1-pyrrolidinyl)-1-pentanone (α-PVP); α-pyrrolidinohexiophenone (α-PHP); α-pyrrolidinoheptiophenone (α-PHpP, PV8); diethylpropion; pyrovalerone; dimethylcathinone; diethylcathinone; methcathinone; ethcathinone; 3-methylmethcathinone (3-MMC); 4-methylethcathinone (4-MEC); 3-chloromethcathinone (3-CMC); 4-chloromethcathinone (4-CMC); n-ethyl-nor-pentedrone (NEP); 3,4-methylenedioxy-α-pyrrolidinobutiophenone (MDPBP); 4-methyl-α-pyrrolidinobutiophenone (MEPBP); 4-fluoromethcathinone (4-FMC); n-ethyl-nor-hexedrone (Hexen); n-ethyl-nor-heptedrone; 4-ethylpentedrone; 4-methyl-NEP; and n-ethyl-nor-pentylone.

In specific embodiments, the target molecule is selected from adenosine, cocaine, glucose, dopamine, serotonin, ochratoxin A, and mephedrone.

In one embodiment, the subject invention provides a kit for detecting a target, comprising the E-AB of the subject invention. The kit can further comprise instructions for using the kit. In some embodiments, the kit may comprise other reagents suitable for detecting the target molecule. The reagents may include buffers and stabilizing agents.

As used herein, the singular forms "a," "an," and "the" are intended to include the plural forms as well, unless the context clearly indicates otherwise. Further, to the extent that the terms "including," "includes," "having," "has," "with," or variants thereof are used in either the detailed description and/or the claims, such terms are intended to be inclusive in a manner similar to the term "comprising." The transitional terms/phrases (and any grammatical variations thereof), such as "comprising," "comprises," and "comprise," can be used interchangeably.

The phrases "consisting of" or "consists essentially of" indicate that the claim encompasses embodiments containing the specified materials or steps and those that do not materially affect the basic and novel characteristic(s) of the claim. Use of the term "comprising" contemplates other embodiments that "consist of" or "consisting essentially of" the recited component(s).

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 0-20%, 0 to 10%, 0 to 5%, or up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated the term "about" meaning within an acceptable error range for the particular value should be assumed. In the context of compositions containing amounts of concentrations of ingredients where the term "about" is used, these values include a variation (error range) of 0-10% around the value ($X \pm 10\%$).

When ranges are used herein, such as for dose ranges, combinations and subcombinations of ranges (e.g., subranges within the disclosed range), specific embodiments therein are intended to be explicitly included.

EXAMPLES

MATERIALS AND METHODS

Materials. Potassium chloride, magnesium chloride, sodium chloride, monosodium phosphate, disodium phosphate, Trizma pre-set crystals (Tris buffer, pH 7.4), tris(2-carboxyethyl) phosphine chloride, 6-mercapto-1-hexanol, cocaine hydrochloride, adenosine, sodium hydroxide, sulfuric acid (95-98%), and calf serum were purchased from Sigma-Aldrich. 3',4'-methylenedioxypyrovalerone chloride (MDPV) was purchased from Cayman Chemicals. All solutions were prepared using Milli-Q (Millipore) water with resistivity of 18.2 MΩ×cm unless specified otherwise. Thiolated methylene blue-modified aptamers were synthesized by Biosearch Technologies and purified with dual-HPLC. All other unmodified oligonucleotides were purchased from Integrated DNA Technologies with HPLC purification and dissolved in PCR-grade water. Oligonucleotide concentrations were measured using a NanoDrop 2000 spectrophotometer.

The names and sequences of DNA oligonucleotides used are as follows:
ADE-25: 5'-CCTGGTGGAGTATTGCGGGGGAAGG-3' (SEQ ID NO: 1)
COC-32: 5'-AGACAAGGAAAATCCTTCAAT-GAAGTGGGTCT-3' (SEQ ID NO: 2)
SC-34: 5'-ACCTTAAGTGGGGTTCGGGTGGAGTT-TATGGGGT-3' (SEQ ID NO: 3)
ADE-25-MB: 5'-SH-C6-CCTGGTGGAGTATTGCGGGG-GAAGG-MB-3' (SEQ ID NO: 4)
COC-32-MB: 5' -SH-C6-AGACAAGGAAAATCCTT-CAATGAAGTGGGTCT-MB-3' (SEQ ID NO: 5)
SC-34-MB: 5'-SH-C6-ACCTTAAGTGGGGTTCGGGTG-GAGTTTATGGGGT-MB-3' (SEQ ID NO: 6)
(SH=thiol group, MB=methylene blue)

Buffers employed were as follows:
High-salt PBS: 1.6 mM $NaH_2PO_4$, 8.4 mM $Na_2HPO_4$, 1 M NaCl, 1 mM $MgCl_2$, pH 7.2

Low-salt PBS: 1.9 mM $NaH_2PO_4$, 8.1 mM $Na_2HPO_4$, 1.9 mM NaCl, 0.5 mM $MgCl_2$, pH 7.4
Low-salt Tris buffer: 10 mM Tris—HCl buffer, 20 mM NaCl, 0.5 mM $MgCl_2$, pH 7.4
High-salt Tris buffer: 10 mM Tris—HCl buffer, 1 M NaCl, 1 mM $MgCl_2$, pH 7.4

Fabrication of E-AB sensors. Gold disk electrodes (2 mm diameter) were purchased from CH Instruments and cleaned. First, the electrode was polished on microcloth (Buehler) with 1-μm diamond suspension (BASi) and 0.05-μm gamma alumina suspension (Buehler). Each polishing step was followed by sonication in ethanol and distilled water for 5 min. Then, the electrode was electrochemically cleaned with a series of voltammetric scans performed in 0.5 M sodium hydroxide, 0.5 M sulfuric acid, and 0.1 M sulfuric acid solutions. To prepare the aptamers for electrode modification, the disulfide groups on the 5'-end of the thiolated, methylene blue-modified aptamers were reduced by incubation in 100 mM tris(2-carboxyethyl) phosphine chloride for 2 h in the dark at room temperature. The aptamers were then diluted to various concentrations (15-200 nM) in high-salt PBS, low-salt PBS with different pH values (pH=6.0, 7.0, 7.4, or 8.0), or low-salt Tris buffer with or without their respective target. The cleaned electrodes were rinsed with distilled water, dried with nitrogen, and immediately incubated in a solution of either aptamer or aptamer-target complexes for 13 h in the dark at room temperature. The electrodes were then backfilled with 1 mM 6-mercapto-1-hexanol solution containing the same concentration of respective target used in the previous step for 2 h at room temperature. Finally, the aptamer-modified electrodes were thoroughly washed with deionized water and then stored in 10 mM Tris (pH 7.4) at room temperature before performing electrochemical measurements.

Electrochemical measurements. All electrochemical measurements were carried out using a CHI760D electrochemical workstation (CH Instruments). A three-electrode system was used, including an Ag/AgCl reference electrode, platinum counter electrode, and aptamer-modified gold working electrode. The aptamer surface densities of the modified electrodes were measured via chronocoulometry. Square wave voltammetry (SWV) was performed for the adenosine, cocaine, and MDPV E-AB sensors. Signal gain was calculated using the equation $((I_T - I_0)/I_0) \times 100\%$, where ($I_0$) and ($I_T$) are the SWV peak currents in the absence and presence of target, respectively.

Aptamer affinity measurement via isothermal titration calorimetry (ITC). All ITC experiments were performed with a MicroCal ITC200 instrument (Malvern) at 23° C. A summary of the experimental conditions employed for each experiment is shown in Table 1.

TABLE 1

ITC parameters and conditions used in this work and the calculated $K_D$s. pH of the buffer is 7.4 unless stated otherwise.

| Cell content | Syringe content | Buffer | $K_D$ (μM) |
|---|---|---|---|
| 20 μM SC-34 | 400 μM (−)-MDPV | Low-salt Tris | 0.33 ± 0.04 |
| 20 μM SC-34 | 400 μM (−)-MDPV | Low-salt PBS | 0.38 ± 0.03 |
| 20 μM SC-34 | 350 μM (−)-MDPV | Low-salt PBS (pH 6.0) | 0.23 ± 0.02 |
| 20 μM SC-34 | 350 μM (−)-MDPV | Low-salt PBS (pH 7.0) | 0.38 ± 0.02 |
| 20 μM SC-34 | 350 μM (−)-MDPV | Low-salt PBS (pH 7.4) | 0.56 ± 0.03 |
| 20 μM SC-34 | 350 μM (−)-MDPV | Low-salt PBS (pH 8.0) | 0.69 ± 0.03 |

TABLE 1-continued

ITC parameters and conditions used in this work and the calculated $K_D$s.
pH of the buffer is 7.4 unless stated otherwise.

| Cell content | Syringe content | Buffer | $K_D$ (μM) |
|---|---|---|---|
| 20 μM SC-34 | 300 μM (−)-MDPV | High-salt Tris | 1.80 ± 0.05 |
| 20 uM SC-34 | 200 μM (−)-MDPV (2×, back-to-back) | High-salt PBS | 1.50 ± 0.04 |
| 20 μM COC-32 | 800 μM cocaine | Low-salt Tris | 5.8 ± 0.3 |
| 20 μM COC-32 | 800 μM cocaine | Low-salt PBS | 5.9 ± 0.3 |
| 80 μM COC-32 | 4000 μM cocaine | High-salt PBS | 70.4 ± 0.8 |
| 20 μM ADE-25 | 1200 μM adenosine (2×, back-to-back) | Low-salt Tris | $K_{D1}$ = 7.4 ± 0.1<br>$K_{D2}$ = 103 ± 0.5<br>$K_{1/2}$ = 27.6 ± 0.2 |
| 20 μM ADE-25 | 2500 μM Adenosine | High-salt PBS | $K_{D1}$ = 36.7 ± 2.4<br>$K_{D2}$ = 14.5 ± 0.6<br>$K_{1/2}$ = 23.1 ± 0.8 |

In each experiment, the sample cell was loaded with an aptamer solution (final concentrations: 20 μM or 80 μM for COC-32, 20 μM for ADE-25, 20 μM for SC-34) and the syringe was loaded with the respective target (final concentrations: 800 μM or 4,000 μM cocaine, 2,500 μM adenosine, 200 or 400 μM (−)–MDPV). Titrations involving COC-32 and SC-34 consisted of an initial purge injection of 0.4 μL followed by 19 successive injections of 2 μL, with a spacing of either 120 s or 180 s between each injection. Titrations involving ADE-25 consisted of an initial 0.4 μL purge injection followed by 38 successive 1 μL injections with a spacing of 120 s between each injection. For all experiments, if saturation was not reached after one series of injections, a second set of injections was performed in the same fashion after reloading the syringe with the target. The raw data were first corrected based on the dilution heat of each target and then analyzed with the MicroCal analysis kit integrated into Origin 7 software, with a single-site binding model for COC-32 and SC-34 or a two-site sequential binding model for ADE-25.

EXAMPLE 1—Rationale for enhancing E-AB sensor performance by controlling microscale probe spacing.

E-AB sensors utilize structure-switching aptamers, which undergo conformational changes when binding to a target. The termini of these aptamers are labeled with a thiol group for immobilization onto a gold electrode surface via thiol-gold bonding and an electroactive redox molecule such as methylene blue for electrochemical reporting. Most E-AB sensors are fabricated using aptamer immobilization in high ionic strength phosphate-buffered saline (pH 7.2) containing 1 M NaCl and 1 mM $MgCl_2$ (high-salt PBS). High ionic strength buffers allow for high loading efficiencies of oligonucleotides on gold surfaces, because the negatively charged phosphate groups of the aptamers are shielded from each other by the relatively high concentration of cations. As a consequence, however, the aptamers are highly flexible with low persistence lengths, and immobilize onto the electrode surface as both individual probes with low inter-oligonucleotide proximities as well as clusters of probes.

Theoretically, limited spacing between aptamer probes imposes restrictions on target recognition and folding that can thus affect signal transduction. The average spacing between aptamers on the electrode surface can be tuned at the macroscopic level by simply altering the quantity of aptamer used for immobilization. However, it is not possible to control local aptamer spacing at the microscale in order to maximize the number of active probes with optimal spacing for target binding and signaling and avoid the formation of dense clusters of inactive probes. Altering average surface densities alone also cannot overcome probe bundling, which occurs at high ionic strengths. To address this problem, two hypotheses were assessed to improve the robustness and sensitivity of E-AB sensors: 1) inter-oligonucleotide spacing can be optimized by immobilizing aptamer-target complexes rather than the aptamer alone, and 2) bundling effects can be minimized by performing aptamer immobilization in low rather than high ionic strength conditions.

EXAMPLE 2—Effects of target-assisted aptamer immobilization on E-AB sensor performance.

To test the first hypothesis, E-AB sensors were fabricated from ADE-25, an engineered structure-switching adenosine-binding DNA aptamer. ADE-25 specifically binds to adenosine with micromolar binding affinity ($K_{1/2}$=27.6 ±0.2 μM) (FIG. 1A) in low-salt Tris buffer (10 mM Tris-HCl, 20 mM NaCl, 0.5 mM $MgCl_2$, pH 7.4) but has no affinity for phosphorylated nucleotide analogs such as ATP, ADP, and AMP. E-AB sensors were first prepared using thiolated, methylene blue-modified ADE-25 (ADE-25-MB) alone, and optimized aptamer surface coverage to tune average inter-oligonucleotide spacing by modifying electrodes with different concentrations of aptamer in high-salt PBS. Increases in aptamer concentration in the range of 15-75 nM resulted in monotonic increases in aptamer surface density (FIG. 2A). The sensing performance of these E-AB sensors was then evaluated by performing detection in solutions containing various concentrations of adenosine (0-1,000 μM). The result shows that the current increased with increasing target concentrations (FIG. 2B).

As expected, low signal gain was observed for sensors with very low or very high surface coverage due to insufficient probe loading or probe overcrowding, respectively. Signal gains at all target concentrations increased as surface density increased from 1.89 to 3.77 picomoles/$cm^2$, but a further increase to 11.1 picomoles/$cm^2$ resulted in decreased signal gains (FIG. 2C). The impairment of aptamer functioning at higher surface densities is possibly due to lower inter-oligonucleotide spacing. By immobilizing the aptamer in its target-bound folded state, a self-assembled aptamer monolayer could be produced with optimal microscale spacing for target recognition and signaling relative to unbound flexible aptamers, which are arbitrarily spaced on the surface in a non-optimized fashion.

Figure 4A:
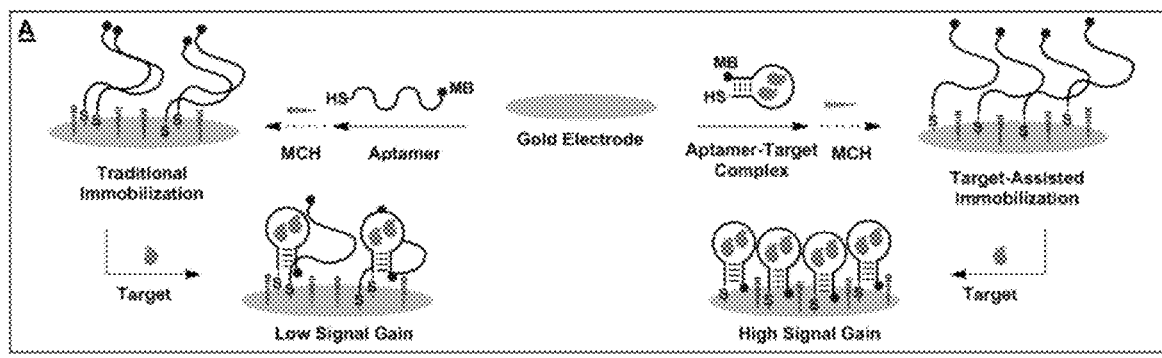
FIGS. 4A-4C show E-AB sensor performance using electrodes modified with an aptamer either alone or bound to the target. (A) Modification of a gold electrode using either the traditional immobilization protocol (left) or our target-assisted immobilization strategy (right). Square-wave voltammetry (SWV) spectra of electrodes modified with the aptamer-adenosine complex (left) or aptamer alone (middle) in (B) buffer or (C) 50% serum and corresponding calibration curves and linear ranges (right) collected using electrodes prepared with target-assisted aptamer immobilization approach (gray) or the traditional method (black). Error bars represent the standard deviation for three working electrodes from each measurement.

To test this, an electrode was modified using a solution of aptamer-target complexes at the optimal surface coverage determined above. Prior to aptamer immobilization, whether ADE-25 retains the ability to bind adenosine was first determined in high-salt PBS using isothermal titration calorimetry (ITC). The ITC results showed that ADE-25 binds adenosine with an affinity ($K_{1/2}$) of 23.1 ±0.8 μM under these conditions (FIG. 1B). Based on this affinity measurement, it can be estimated that ~91% of the aptamer is bound to the target in the presence of 250 μM adenosine (FIG. 3). For electrode fabrication, a solution containing 25 nM freshly-reduced ADE-25-MB was first prepared in high-salt PBS with 250 μM adenosine and then the electrodes were submerged in the aptamer-target complex solution (FIG. 4A, right). Afterwards, the electrodes were cleaned thoroughly with buffer to remove any residual adenosine.

Figure 4B:
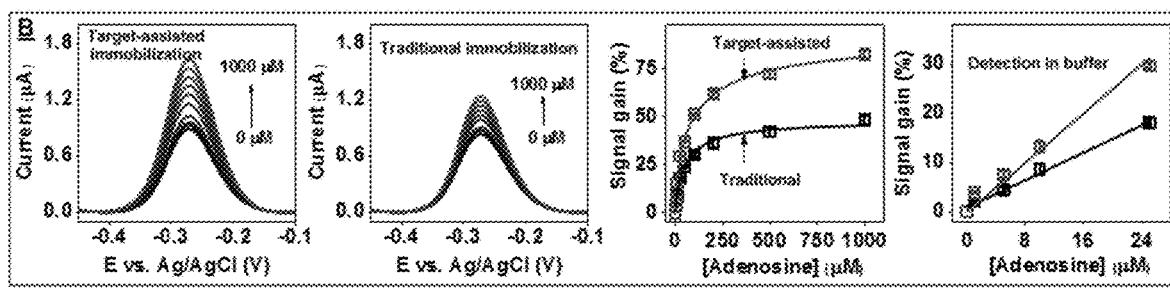
Figure 4C:
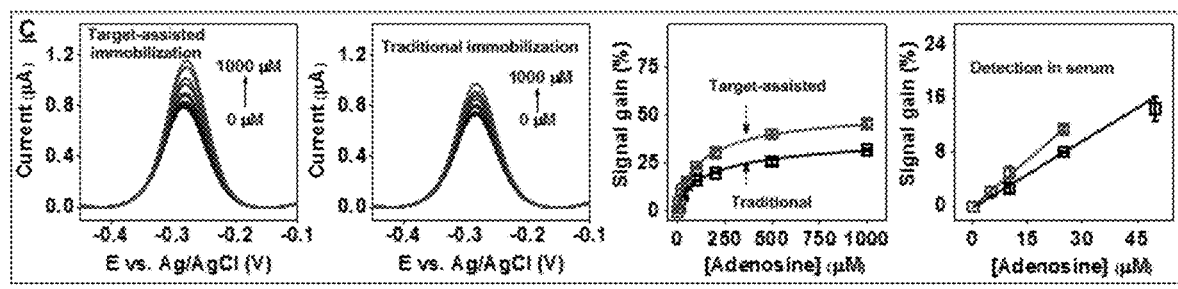
Figure 5:
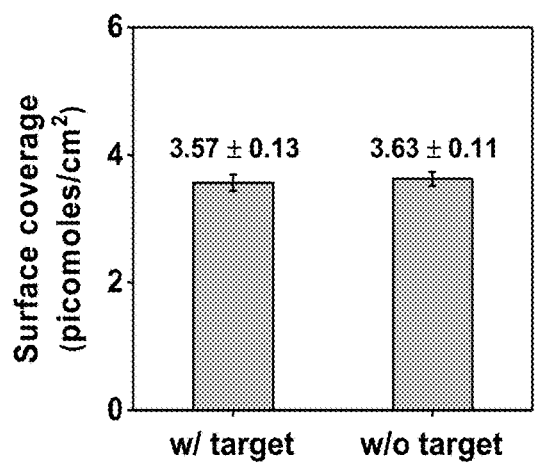
FIG. 5 shows aptamer surface coverages of electrodes fabricated by immobilizing the aptamer in the presence or absence of 250 μM adenosine. Error bars represent the standard deviation of measurements from three independently fabricated electrodes.

As a control, another set of gold electrodes modified with 25 nM ADE-25-MB alone was prepared using a tradition immobilization approach (FIG. 4A, left). Both sets of electrodes had virtually the same average surface density (FIG. 5). However, electrodes modified via target-assisted aptamer immobilization yielded higher signal-to-noise ratio and had a lower LOD than electrodes modified with aptamer alone in both buffer (LOD=1 μM vs. 5 μM) and 50% serum (LOD=5 μM vs. 10 μM) (FIGS. 4B-4C). Since the total amount of aptamer immobilized on both electrodes was essentially identical, the observed improvement in sensing performance can be most likely be attributed to optimized inter-oligonucleotide spacing.

EXAMPLE 3—Confirmation of the generalizability of target-assisted aptamer immobilization.

To demonstrate whether target-assisted aptamer immobilization can improve the performance of E-AB sensors regardless of the aptamer sequence and structure, sensors were fabricated with a known three-way-junction-structured cocaine aptamer with structure-switching functionality (COC-32). Electrodes with the thiolated, methylene-blue labeled version of this aptamer (COC-32-MB) was prepared in the absence or presence of cocaine (250 µM) in high-salt PBS. Once again, although both sets of electrodes displayed similar aptamer surface densities (FIG. 6A), the sensors prepared via target-assisted aptamer immobilization demonstrated greater signal gains at all tested concentrations of cocaine (0-1,000 µM) (FIGS. 6B-6D) and improved LODs relative to electrodes modified with aptamer alone (LOD=1 µM vs. 2 µM) (FIG. 6E). This confirmed that target-assisted aptamer immobilization generally enhances the performance of E-AB sensors.

EXAMPLE 4—Relationship between the concentration of aptamer-target complex used for electrode modification and E-AB sensor performance.

Figure 8:
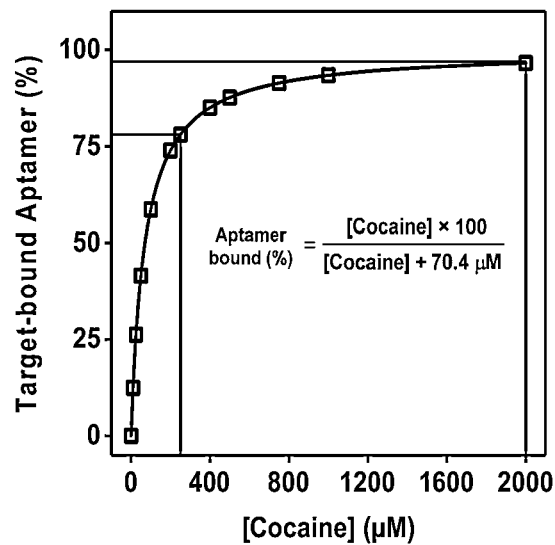
FIG. 8 shows the simulated binding curve for COC-32 based on its affinity for cocaine in high-salt PBS ($K_D$=70.4 μM). The blue lines indicate that ~78% and 96% of the aptamer is bound in the presence of 250 μM and 2 mM cocaine, respectively.
Figure 9:
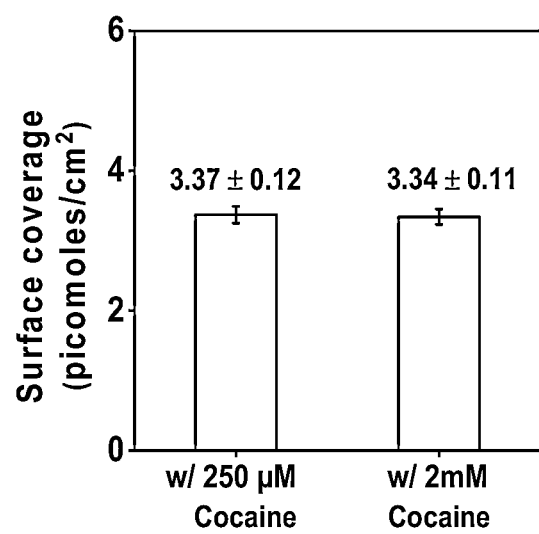
FIG. 9 shows the surface coverage of electrodes modified with COC-32-MB via target-assisted immobilization in high-salt PBS in the presence of 250 μM or 2 mM cocaine. Error bars represent the standard deviation of measurements from three different electrodes.

The cocaine-binding aptamer has weak affinity for its target at high salt concentrations, which is confirmed via ITC that COC-32 binds cocaine with a $K_D$ of 70.4±0.8 µM in the high-salt PBS buffer commonly used for aptamer immobilization (FIG. 7A). In these conditions, only ~78% of the aptamer is bound to the target in the presence of 250 µM cocaine (FIG. 8), such that the resulting monolayer would be predicted to contain both active and inactive, non-optimally-spaced probes. The hypothesis is that maximizing the quantity of target-bound aptamer during the aptamer immobilization process would result in the greatest quantity of immobilized active aptamers, thereby yielding the best attainable sensor performance. E-AB sensors were, therefore, fabricated by immobilizing COC-32-MB in the presence of 2 mM cocaine, where ~96% of the aptamer is in the target-bound state (FIG. 8). Although electrodes prepared in the presence of 250 µM or 2 mM cocaine had the same aptamer surface densities (FIG. 9), the latter sensors yielded higher signal-to-noise ratios at all target concentrations—especially in the range from 100-1,000 µM cocaine, where an 8% improvement in signal gain was seen (FIG. 10). This clearly demonstrates that more active aptamer probes were being immobilized on the electrode surface with immobilization solutions containing a higher proportion of aptamer-target complexes.

EXAMPLE 5—Dependency of E-AB sensor performance on the ionic strength of the immobilization buffer.

Having determined that target-assisted aptamer immobilization improves E-AB sensor performance, the hypothesis on the relationship between the ionic strength of the electrode modification buffer and E-AB sensor performance was next tested. Local inter-oligonucleotide distances can be increased and probe bundling can be mitigated by decreasing the ionic strength of the buffer used for probe immobilization. To evaluate this, electrodes with COC-32-MB alone were modified in either high-salt PBS or low-salt PBS (10 mM PBS, 1.9 mM NaCl, 0.5 mM $MgCl_2$, pH 7.4). To ensure that the electrodes had similar surface densities, a greater concentration of aptamer was used for immobilization in the low ionic strength buffer. Although both electrodes had similar surface densities (FIG. 11A), electrodes prepared in low-salt PBS had improved signal gain in the range of 50-1,000 µM cocaine (FIGS. 11B-11D). This indicates that the improvement in E-AB performance was most likely due to the mitigation of aptamer bundling and resulting increase in active probes on the electrode surface when lower ionic strength buffer was used.

Figure 12:
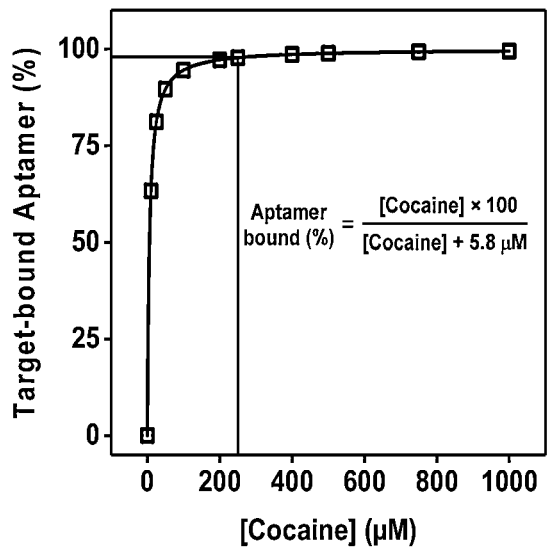
FIG. 12 shows the simulated binding curve for COC-32 based on the affinity for cocaine in low-salt PBS ($K_D$=5.8 μM). The blue lines indicate that 96% of the aptamer is bound in the presence of 250 μM cocaine.
Figure 13:
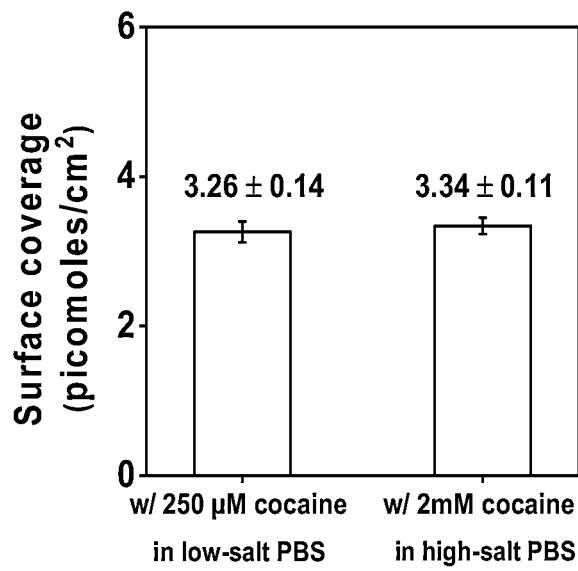
FIG. 13 shows the surface coverage of electrodes modified with COC-32-MB via target-assisted immobilization in low-salt PBS with 250 μM or in high-salt PBS with 2 mM cocaine. Error bars represent the standard deviation of measurements from three different electrodes.
Figure 19A:
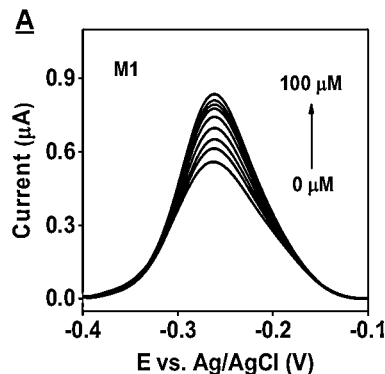
FIGS. 19A-19D show electrodes fabricated using SC-34-MB via target-assisted aptamer immobilization with various concentrations of MDPV. SWV for electrodes modified with SC-34-MB in the presence of (A) 0 μM, (B) 5 μM, (C) 10 μM, and (D) 50 μM MDPV after challenging with 0-100 μM MDPV.
Figure 19B:
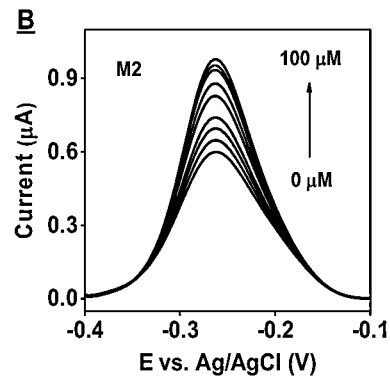
Figure 19C:
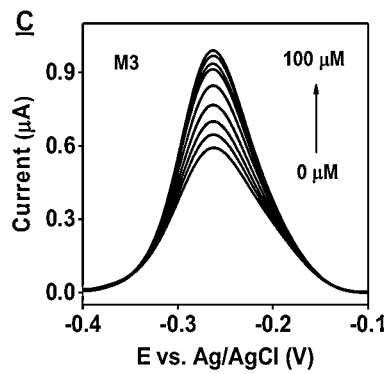
Figure 19D:
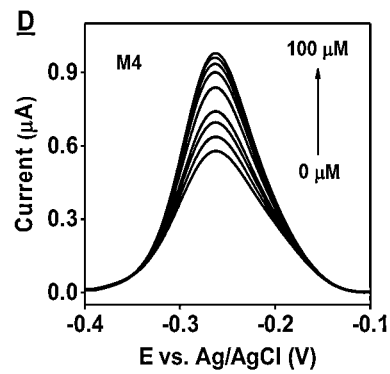

Whether the addition of target-assisted immobilization would further improve sensor performance was then determined. Electrodes were modified with COC-32-MB in low-salt PBS containing 250 µM cocaine as well as in high-salt PBS containing 2 mM cocaine as a control. In both cases, ~96% of the aptamer is bound to cocaine based on the target affinity of the aptamer (high-salt PBS $K_D$=70.4 ±0.8 µM; low-salt PBS $K_D$=5.8 ±0.3) (FIGS. 7A-7B) and the target concentration employed (FIGS. 8 and 12). Despite both sets of electrodes having similar surface coverages (FIG. 13), great improvements were observed in signal-to-noise ratio from electrodes immobilized with the aptamer in low ionic strength conditions, with approximately 10% improvement in signal gain in the concentration range of 50-1,000 µM cocaine (FIGS. 14A-14C).

Given that both experiments demonstrated equivalent surface coverage and similar proportions of aptamer-target complexes for modification (~96%), the improvement in performance can be primarily attributed to the predominance of active aptamers on the electrode surface when the ionic strength of the immobilization buffer was reduced. These results confirm that buffer ionic strength has a significant effect on the performance of E-AB sensors.

EXAMPLE 6—Effect of the type of buffering system used for aptamer immobilization on E-AB sensor performance.

Changing the buffering system used for aptamer immobilization should not affect the performance of the resultant E-AB sensors if the ionic strength and pH remains the same. To confirm this, electrodes were modified with COC-32-MB in the presence of 250 µM cocaine in either low-salt Tris buffer or low-salt PBS with the same ionic strength and pH. At the same aptamer surface coverage (FIG. 15A), both sensors exhibited similar performance (FIGS. 15B-15C and FIG. 14C) due to the equivalent binding affinity of COC-32-MB for cocaine in both buffers (FIGS. 7B-7C).

Finally, the performance of sensors prepared via target-assisted aptamer immobilization in low-salt Tris buffer versus conventionally prepared electrodes for the detection of cocaine in complex biosamples was compared. The results show that electrodes modified using the present method demonstrated higher signal-to-noise ratios and greater sensitivity in 50% saliva relative to conventionally modified electrodes (LOD=2 µM vs. 4 µM) (FIGS. 14D-14G, and FIG. 16).

EXAMPLE 7—Target-assisted immobilization is effective independent of aptamer sequence, structure, and affinity.

As a final demonstration of the generalizability of the present method, electrodes were prepared using SC-34, a G-rich, high-affinity structure-switching DNA aptamer that binds the synthetic cathinone 3',4'-methylenedioxypyrovalerone (MDPV) with a $K_D$ of 300 nM (for (−)–MDPV) in low-salt Tris buffer. Gold electrodes were modified with the thiolated, methylene blue-modified version of SC-34 (SC-34-MB) in low-salt Tris buffer in the absence or presence of 5, 10 or 50 µM MDPV, respectively corresponding to 94%, 97%, 99% aptamer-target complex in solution (FIG. 17). Increases in the concentration of MDPV during electrode modification resulted in slightly decreased aptamer surface coverage (FIG. 18A). This is probably because the rigid aptamer-target complex occupies more space than the unbound aptamer, and thus slightly increasing the quantity of the complex results in lower surface coverage.

Figure 20A:
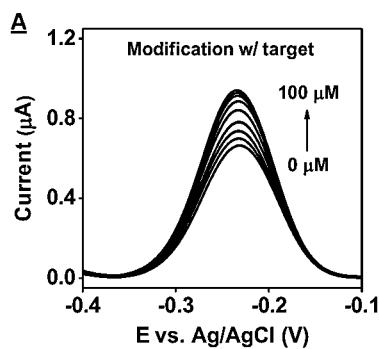
FIGS. 20A-20C show detection of MDPV in 50% urine using electrodes modified with SC-34-MB via (A) target-assisted immobilization in low-salt Tris buffer with 50 μM MDPV or (B) conventional means in high-salt PBS. (C) Calibration curves derived from spectra shown in A (gray) and B (black). Error bars represent the standard deviation of measurements from three independently fabricated electrodes.
Figure 20B:
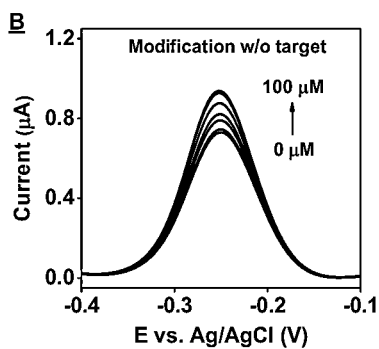
Figure 20C:
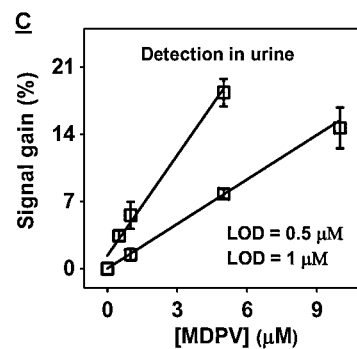

Nevertheless, electrodes modified with aptamer-MDPV complexes consistently yielded higher signal gains at all tested target concentrations compared to electrodes modified with the aptamer alone (FIG. 18B and FIG. 19). However, increasing the MDPV concentration beyond 5 µM during the modification step yielded no more than a 5% improvement in signal gain (at 100 µM MDPV), most likely because most aptamers (~94%) are already bound to target at 5 µM MDPV. Using 50 µM MDPV for target-assisted aptamer immobilization, similar improvements were also observed in sensitivity for MDPV detection in 50% urine (LOD=0.5 µM vs 1 µM) (FIG. 18C and FIG. 20).

The results then confirmed that the buffer system employed for aptamer immobilization has no effect on sensor performance in low-salt buffer; electrodes modified in either low-salt Tris buffer or PBS had nearly the same response at all tested target concentrations (FIGS. 18D and 18F). This is probably because the aptamer has the same $K_D$ (~300 nM) in both buffers, as confirmed by ITC (FIGS. 21A-21B).

Finally, to confirm that the ionic strength used during target-assisted aptamer immobilization effects E-AB sensing performance, electrodes modified with SC-34-MB were fabricated in either low-salt or high-salt PBS in the presence of 50 µM MDPV. In both buffers, ≥97% of the aptamer was bound to MDPV (FIGS. 17 and 22). Based on ITC, the aptamer's $K_D$ in high-salt PBS is 1.50 ±0.04 µM (FIG. 21C). Although both sets of electrodes had similar surface coverage (FIG. 23A), electrodes modified in low-salt PBS were more sensitive than those modified in high-salt PBS (LOD=0.1 µM vs. 0.5 µM) (FIGS. 18E-18G, and FIG. 23B).

Finally, the results confirmed that immobilization buffer type also had no effect on E-AB sensor performance with high-salt condition. Specifically, electrodes were modified with SC-34-MB in high-salt Tris buffer in the absence and presence of 50 µM MDPV and challenged the resulting sensors with 0-100 µM MDPV. Although both sets of electrodes had similar surface coverages (FIG. 24A), electrodes modified via target-assisted immobilization yielded higher signal gains (FIG. 24B) and demonstrated lower limits of detection than traditionally-modified electrodes (FIG. 24C). These results further support the conclusion that target-assisted aptamer immobilization results in E-AB sensors with improved sensing performance.

Figure 25:
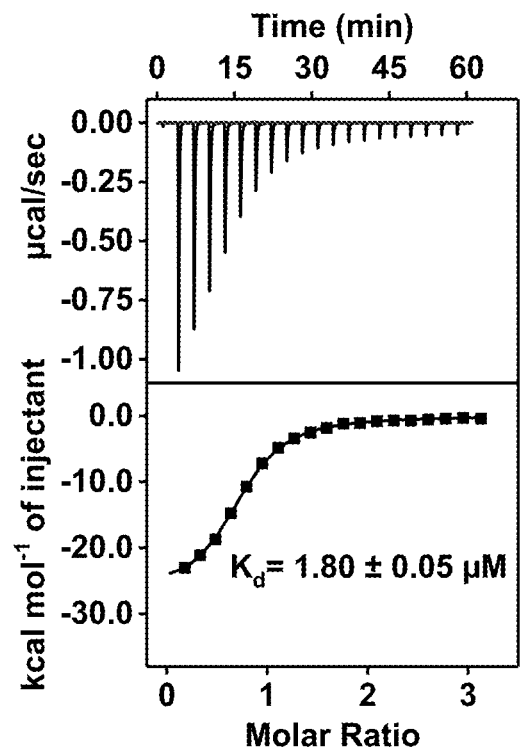
FIG. 25 shows ITC characterization of SC-34 affinity for (−)−MDPV in high-salt Tris buffer. Top panels present raw data, showing the heat generated from each titration of (−)−MDPV to SC-34, while bottom panels show the integrated heat of each titration after correcting for dilution heat of the titrant. ITC data were fitted with a single-site binding model.

Notably, electrodes modified via target-assisted aptamer immobilization in high-salt Tris buffer or PBS exhibited similar performance (FIG. 18F). ITC confirmed that the binding affinity of SC-34 was similar in high-salt PBS (FIG. 21C, $K_D$=1.50±0.05 µM) and high-salt Tris buffer (FIG. 25, $K_D$=1.80±0.04 µM), demonstrating that the use of different immobilization buffer systems does not affect sensor performance. These results further support the conclusion that sensor performance was primarily improved due to increased inter-oligonucleotide spacing and minimization of strand 'bundling' in the low ionic strength buffer during modification.

EXAMPLE 8—Effect of buffer pH used for aptamer immobilization on E-AB sensor performance.

Figure 26:
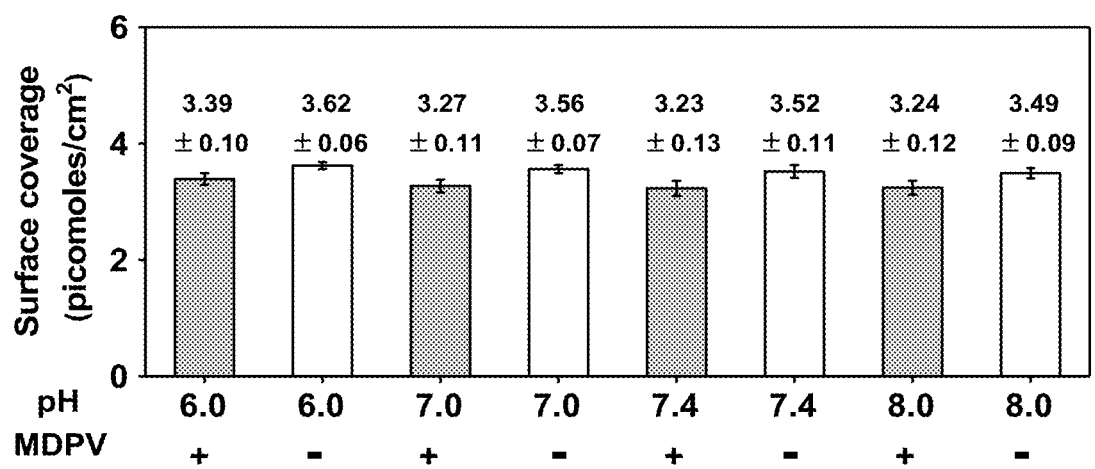
FIG. 26 shows aptamer surface coverages of electrodes fabricated with SC-34-MB in the absence (white bars) or presence of 50 μM MDPV (gray bars) in low-salt PBS with a pH of 6.0, 7.0, 7.4 or 8.0. Error bars represent the standard deviation of measurements from three independently fabricated electrodes.

The effect of altering the immobilization buffer pH on the performance of the resulting E-AB sensors was tested. As a demonstration, gold electrodes with SC-34-MB were prepared in the absence or presence of 50 µM MDPV in low-salt PBS formulations with the same ionic strengths but different pH values (pH=6.0, 7.0, 7.4, or 8.0). Buffer pH did not significantly affect aptamer surface coverage, although electrodes fabricated via target-assisted immobilization consistently had slightly lower surface coverage (3.28±0.07 pmol/cm$^2$) than those modified via the traditional aptamer immobilization method (3.55±0.06 pmol/cm$^2$) (FIG. 26).

The performance of traditionally-modified electrodes was tested by challenging them with 0-100 µM MDPV. E-AB sensors fabricated at pH 8.0 (FIG. 27A and FIG. 28A) or 7.4 (FIG. 27B and FIG. 28B) produced nearly identical signal gains, while aptamer immobilization at pH 7.0 yielded sensors with only slightly inferior performance (FIG. 27C and FIG. 28C). In contrast, sensors fabricated at pH 6.0 yielded noticeably lower signal gains at all target concentrations (FIG. 27D and FIG. 28D). This may be because the phosphate groups of the aptamers are predominantly singly protonated at this pH, rather than being doubly-protonated as occurs at pH≥7.0. This would result in less electrostatic repulsion between aptamers, thus increasing the likelihood of bundling during immobilization.

The performance of electrodes modified via target-assisted immobilization was then tested. Regardless of immobilization buffer pH, these electrodes consistently yielded higher signal gains and had lower limits of detection compared to traditionally modified electrodes (FIG. 27). Although a similar pattern of pH effects on electrode performance was observed, the magnitude of signal gain was consistently greater after target-assisted immobilization at every pH tested (FIGS. 27A-27D).

Figure 29C:
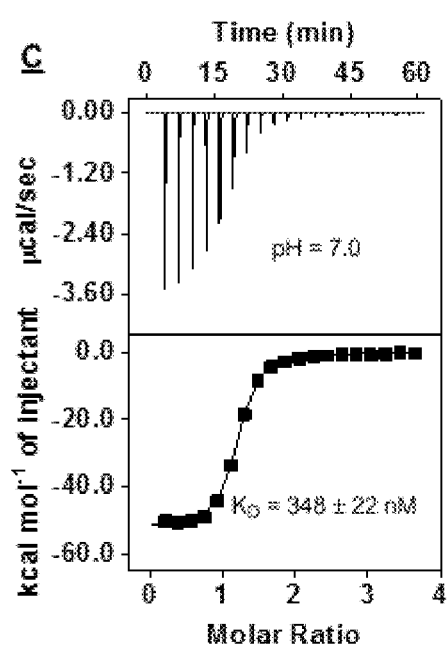
Figure 29D:
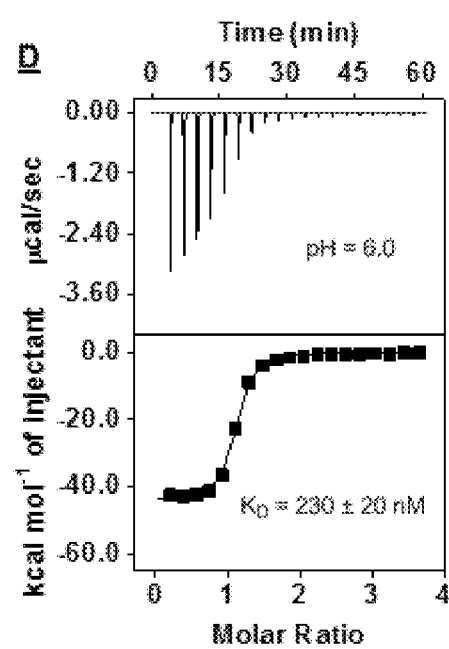

ITC was next used to determine if buffer pH affected sensor performance by affecting the formation and stability of aptamer-target complexes during aptamer immobilization. Specifically, the binding affinity of SC-34 to (−)-MDPV was measured in low-salt PBS at pH 6.0, 7.0, 7.4, or 8.0. In all pH conditions, the binding affinity values did not greatly differ (FIG. 29). This meant that in all buffers containing 50 µM MDPV, ≥97% of the aptamer was bound to the target, indicating that pH did not affect the extent of aptamer-target complexation. The results, therefore, suggest that the use of relatively low-pH buffers for aptamer immobilization promotes aptamer bundling due to reduced electrostatic repulsion, which in turn negatively impacts sensor performance.

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application and the scope of the appended claims. These examples should not be construed as limiting. In addition, any elements or limitations of any invention or embodiment thereof disclosed herein can be combined with any and/or all other elements or limitations (individually or in any combination) or any other invention or embodiment thereof disclosed herein, and all such combinations are contemplated within the scope of the invention without limitation thereto.

We claim:

1. A method for fabricating an electrochemical aptamer-based (E-AB) sensor, the method comprising:
   providing an electrode;
   incubating the electrode with an immobilizing solution comprising aptamer-target complexes each comprising an aptamer bound to an analyte, the immobilizing solution having a low ionic strength;
   contacting the electrode with a solution comprising a backfiller; and
   removing the target from each of the aptamer-target complexes.

2. The method according to claim 1, the electrode being a solid electrode or paper-based electrode, the solid electrode being made of gold, silver, copper, platinum, palladium, an alloy, or a mixture thereof.

3. The method according to claim 1, the electrode being a gold electrode.

4. The method according to claim 1, the aptamer having structure-switching functionality.

5. The method according to claim 1, the ionic strength being from about 1 mM to about 50 mM.

6. The method according to claim 1, the aptamer being modified with a redox tag at one end and a functional group at the other end.

7. The method according to claim 6, the redox tag being methylene blue.

8. The method according to claim 6, the functional group being a thiol, sulfide, disulfide, amide, ester, alkenyl, alkynyl, carbonyl, aldehyde, carboxylate, carboxyl, or carbonate ester group.

9. The method according to claim 6, the functional group being linked to the aptamer via a linker.

10. The method according to claim 9, the linker comprising 1-10 carbon atoms.

11. The method according to claim 1, the aptamer being labeled with a thiol group at the 5' end, and methylene blue redox tag at the 3' end.

12. The method according to claim 1, the backfiller being selected from 6-mercapto-1-hexanol (MCH), dithiothreitol (DTT), 9-mercapto-1-nonanol, 2-{2-[2-(2-mercaptoethoxy)ethoxy]ethoxy}lethanol, and combination thereof.

13. A method for spatial distribution of aptamers on an electrode, the method comprising:
   incubating the electrode with an immobilizing solution comprising aptamer-target complexes each comprising an aptamer bound to an analyte;
   contacting the electrode with a solution comprising a backfiller; and
   removing the target from each of the aptamer-target complexes.

14. The method according to claim 13, the electrode being a solid electrode or paper-based electrode, the solid electrode being made of gold, silver, copper, platinum, palladium, an alloy, or a mixture thereof.

15. The method according to claim 13, the electrode being a gold electrode.

* * * * *

SEQUENCE LISTING

```
Sequence total quantity: 6
SEQ ID NO: 1            moltype = DNA  length = 25
FEATURE                 Location/Qualifiers
misc_feature            1..25
                        note = aptamer
source                  1..25
                        mol_type = other DNA
                        organism = synthetic construct
SEQUENCE: 1
cctggtggag tattgcgggg gaagg                                            25

SEQ ID NO: 2            moltype = DNA  length = 32
FEATURE                 Location/Qualifiers
misc_feature            1..32
                        note = aptamer
source                  1..32
                        mol_type = other DNA
                        organism = synthetic construct
SEQUENCE: 2
agacaaggaa aatccttcaa tgaagtgggt ct                                    32

SEQ ID NO: 3            moltype = DNA  length = 34
FEATURE                 Location/Qualifiers
misc_feature            1..34
                        note = aptamer
source                  1..34
                        mol_type = other DNA
                        organism = synthetic construct
SEQUENCE: 3
accttaagtg gggttcgggt ggagtttatg gggt                                  34

SEQ ID NO: 4            moltype = DNA  length = 25
FEATURE                 Location/Qualifiers
misc_feature            1..25
                        note = aptamer
misc_feature            1
                        note = thiol group with six-carbon spacer
misc_feature            25
                        note = methylene blue tag
source                  1..25
                        mol_type = other DNA
                        organism = synthetic construct
SEQUENCE: 4
cctggtggag tattgcgggg gaagg                                            25

SEQ ID NO: 5            moltype = DNA  length = 32
FEATURE                 Location/Qualifiers
misc_feature            1..32
                        note = aptamer
misc_feature            1
                        note = thiol group with six-carbon spacer
misc_feature            32
                        note = methylene blue tag
source                  1..32
                        mol_type = other DNA
                        organism = synthetic construct
SEQUENCE: 5
agacaaggaa aatccttcaa tgaagtgggt ct                                    32

SEQ ID NO: 6            moltype = DNA  length = 34
FEATURE                 Location/Qualifiers
misc_feature            1..34
                        note = aptamer
misc_feature            1
                        note = thiol group with six-carbon spacer
misc_feature            34
                        note = methylene blue tag
source                  1..34
                        mol_type = other DNA
                        organism = synthetic construct
SEQUENCE: 6
accttaagtg gggttcgggt ggagtttatg gggt                                  34
```